United States Patent
Wanunu et al.

(10) Patent No.: US 10,914,660 B2
(45) Date of Patent: Feb. 9, 2021

(54) APPARATUS AND METHOD FOR OPTOTHERMAL HEATING OF NANOSCALE ENVIRONMENTS

(71) Applicant: Northeastern University, Boston, MA (US)

(72) Inventors: Meni Wanunu, Needham, MA (US); Hirohito Yamazaki, Brighton, MA (US)

(73) Assignee: Northeastern University, Boston, MA (US)

( * ) Notice: Subject to any disclaimer, the term of this patent is extended or adjusted under 35 U.S.C. 154(b) by 0 days.

(21) Appl. No.: 16/475,491

(22) PCT Filed: Jan. 8, 2018

(86) PCT No.: PCT/US2018/012846
§ 371 (c)(1),
(2) Date: Jul. 2, 2019

(87) PCT Pub. No.: WO2018/129484
PCT Pub. Date: Jul. 12, 2018

(65) Prior Publication Data
US 2019/0339177 A1 Nov. 7, 2019

Related U.S. Application Data

(60) Provisional application No. 62/443,316, filed on Jan. 6, 2017.

(51) Int. Cl.
*G01N 1/44* (2006.01)
*B82Y 20/00* (2011.01)
*G02B 6/122* (2006.01)

(52) U.S. Cl.
CPC .............. *G01N 1/44* (2013.01); *B82Y 20/00* (2013.01); *G02B 6/122* (2013.01)

(58) Field of Classification Search
CPC ...... C12Q 1/6816; G01N 1/44; G01K 2211/00
See application file for complete search history.

(56) References Cited

U.S. PATENT DOCUMENTS

| | | | |
|---|---|---|---|
| 2013/0220811 A1* | 8/2013 | Aksimentiev | G01N 27/447 204/454 |
| 2014/0064324 A1* | 3/2014 | Kasianowicz | G01N 25/00 374/45 |

OTHER PUBLICATIONS

Di Fiori et al, "Optoelectronic Control of Surface Charge and Translocation Dynamics in Solid-State Nanopores" Nat. Nanotechnol. Dec. 2013; 8(12):946-51. doi: 10.1038/nnano.2013.221. Epub Nov. 3, 2013. (Year: 2013).*

* cited by examiner

*Primary Examiner* — Thomas L Dickey
(74) *Attorney, Agent, or Firm* — Verrill Dana, LLP

(57) ABSTRACT

An apparatus and a method are provided for selectively and rapidly applying heat to a nanoscale environment in a controlled manner. The technology utilizes laser irradiation of a solid state material to heat a nanoscale point of interest by an optothermal effect. The technology can be used to the tip of an atomic force microscope, a spot on a flat surface, or a nanopore, or molecules in their vicinity. The apparatus and method are capable of rapidly scanning the temperature of a nanoscale object such as a molecule or biomolecular complex and to interrogate properties of the object at high throughput. The methods can be used in nanofabrication processes or to drive single molecule chemistry.

19 Claims, 19 Drawing Sheets

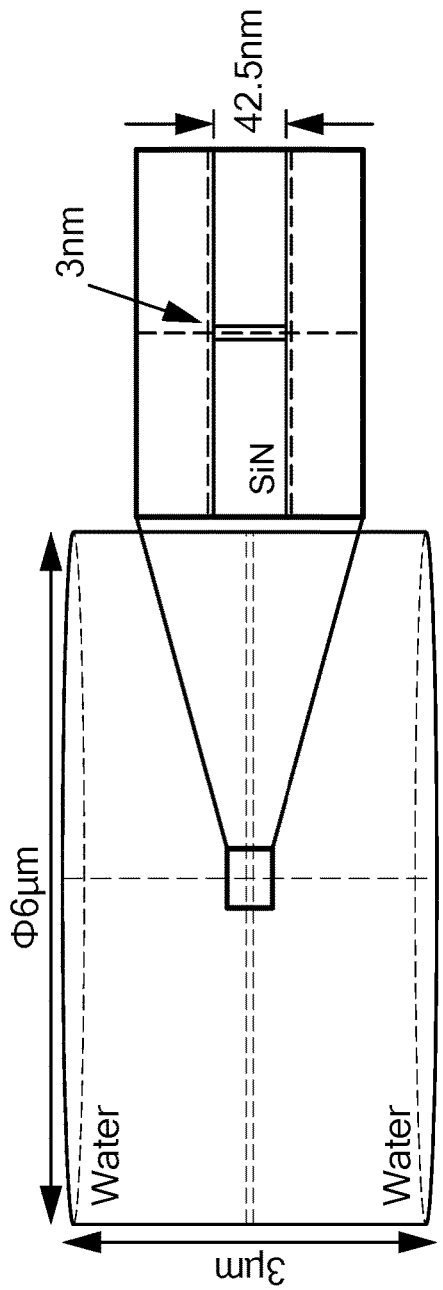
*FIG. 5A*
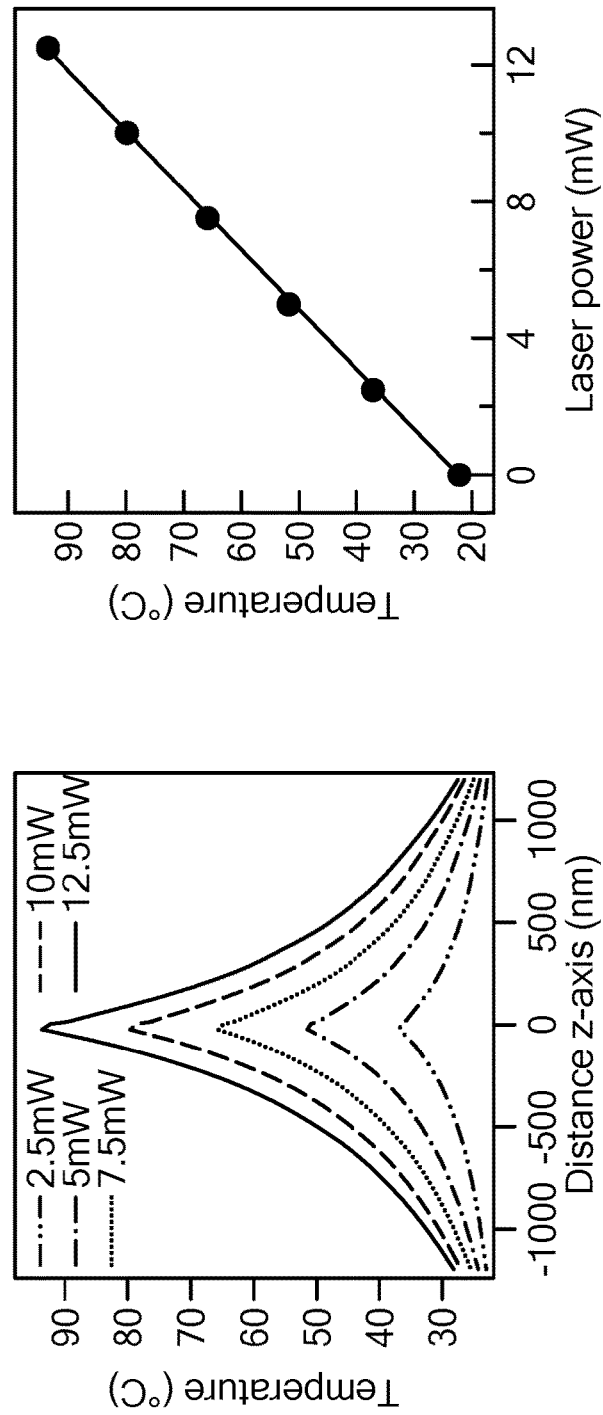
*FIG. 5B*
*FIG. 5C*

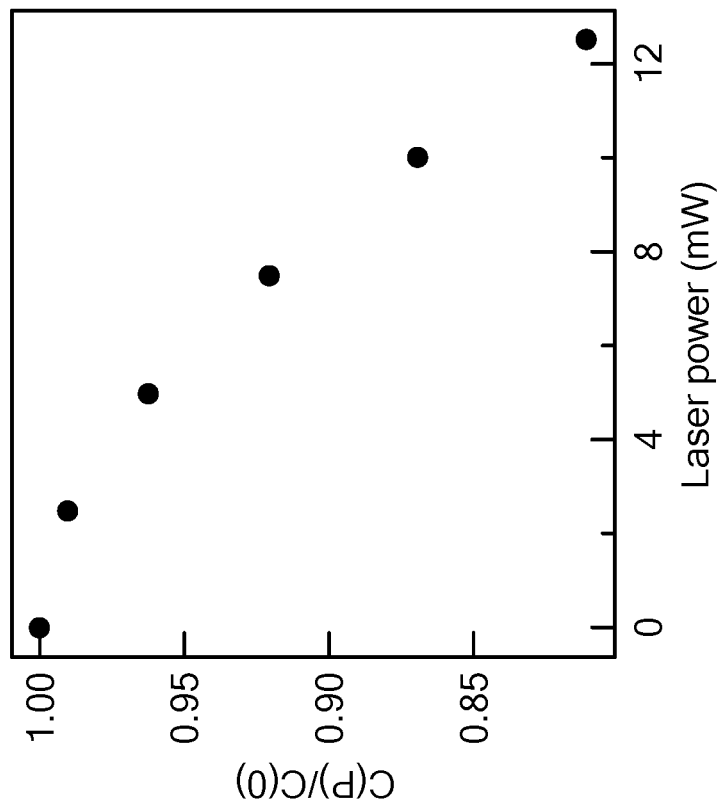
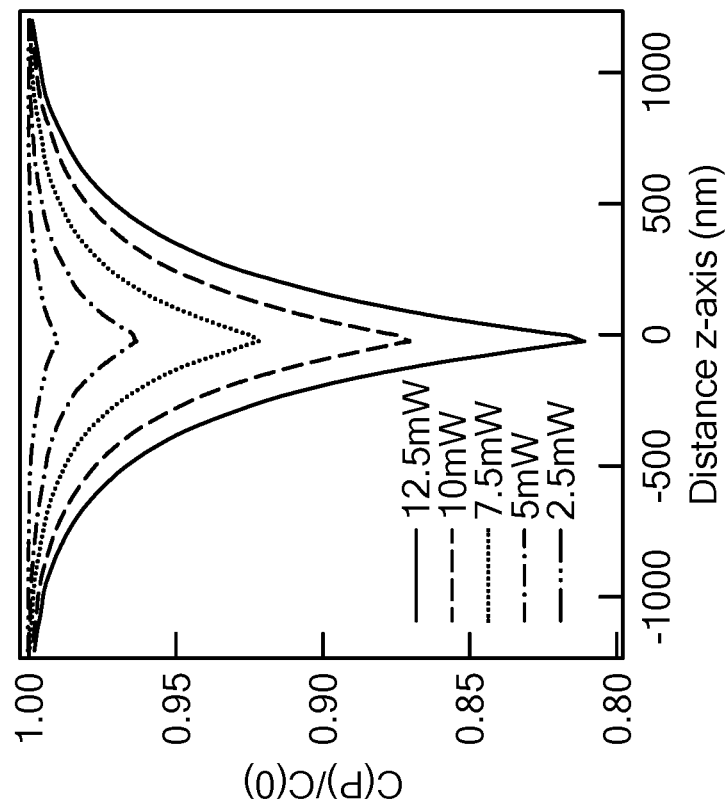
FIG. 6B
FIG. 6A

3WJ-DNA (30°C) - 3WJ30C
A: 5'-GGCAACTTTGATCCCTCGGTTTAGCGCCGGCCTTTTCTCCCACACTTTCACGTTTTCTATCATATTTCAATC
B: 5'-CTAACTATATACTCTTCGTGAAAGTGTGGGAGAAAAGGCCGGCGCTAAACCGAGGGATCAAAGTTGCC
C30: 5'-GAAATATGATAGAAAAGATAGTATATAG

3WJ-DNA (37.5°C) - 3WJ37.5C
A: 5'-GGCAACTTTGATCCCTCGGTTTAGCGCCGGCCTTTTCTCCCACACTTTCACGTTTTCTATCATATTTCAATC
B: 5'-CTAACTATATACTATCTTCGTGAAAGTGTGGGAGAAAAGGCCGGCGCTAAACCGAGGGATCAAAGTTGCC
C37.5: 5'-GATTGAAATATGATAGAATTGATGAGTATATAGTTAG

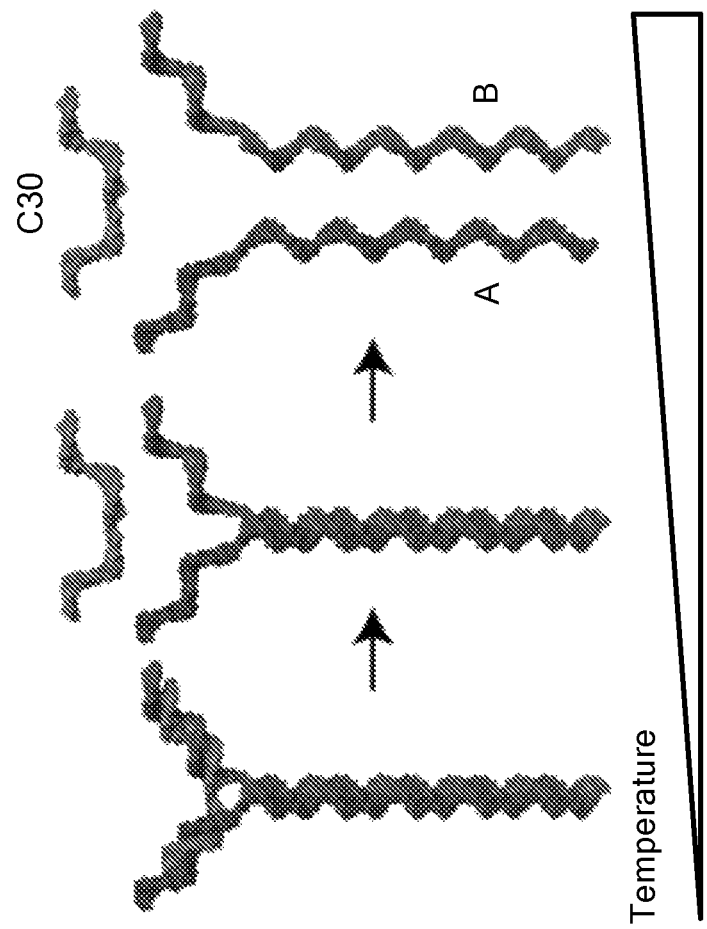

FIG. 7D

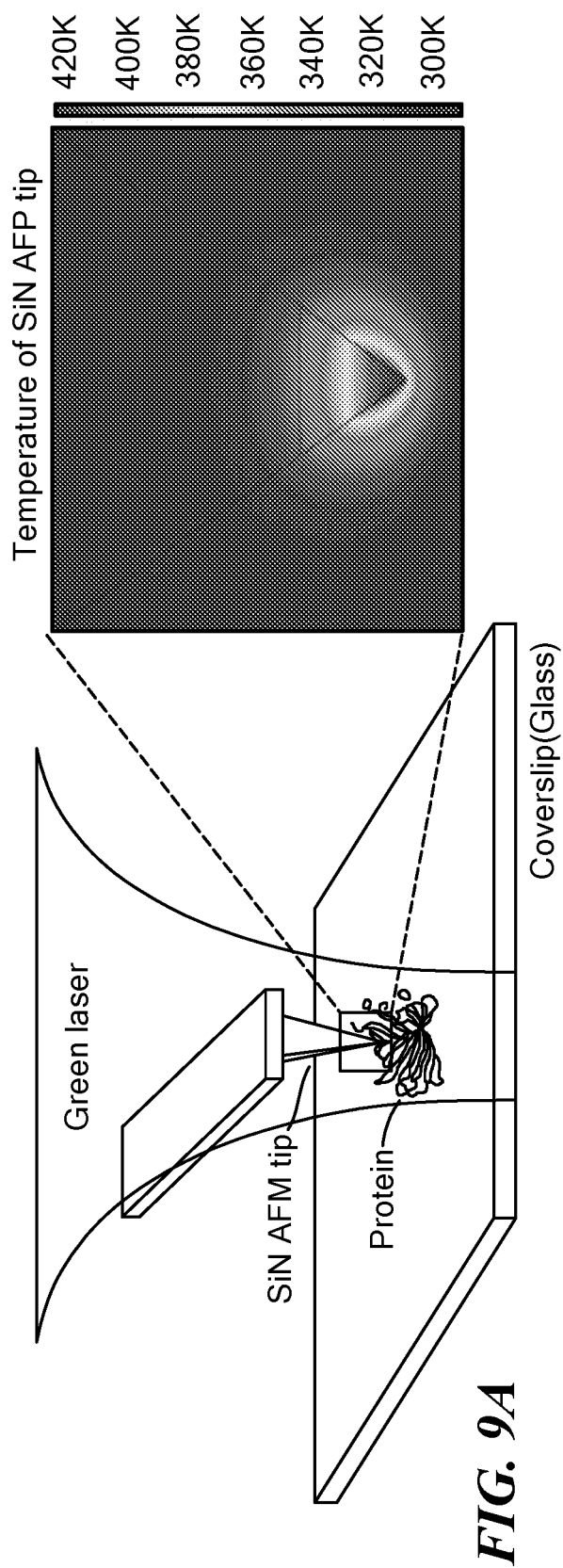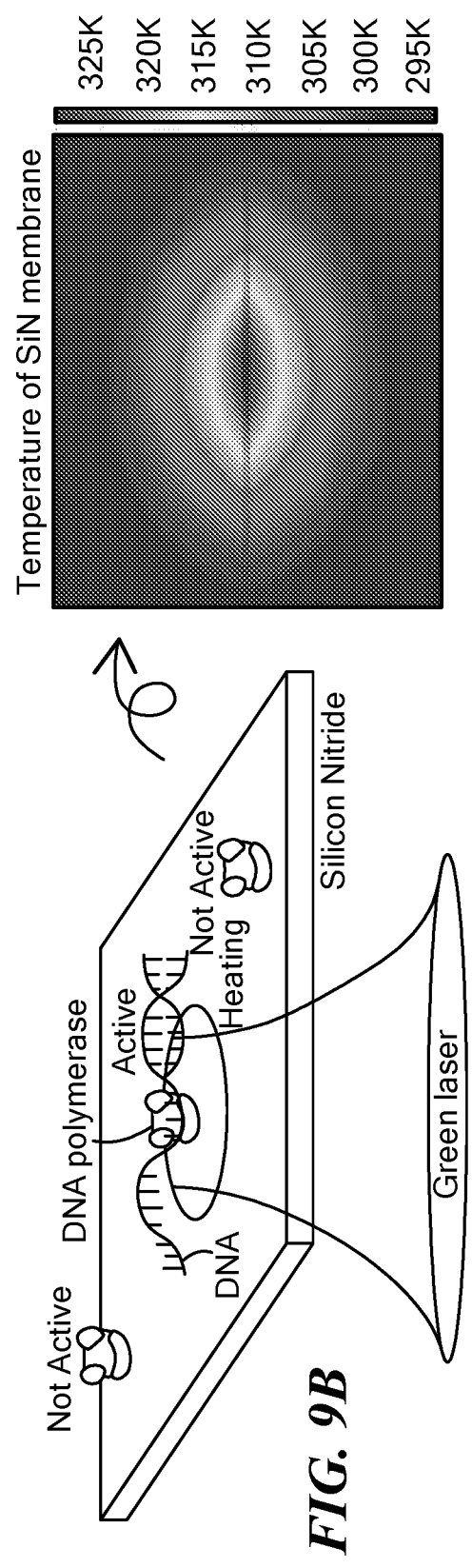
FIG. 9A
FIG. 9B

APPARATUS AND METHOD FOR OPTOTHERMAL HEATING OF NANOSCALE ENVIRONMENTS

CROSS REFERENCE TO RELATED APPLICATIONS

This application claims the priority of U.S. Provisional Application No. 62/443,316 filed 8 Jan. 2017 and entitled "Contactless Optothermal Heating of Silicon Nitride for Instant Temperature Control of Individual Particles, Molecules, and Molecular Complexes Near Surfaces", the whole of which is hereby incorporated by reference.

STATEMENT REGARDING FEDERALLY SPONSORED RESEARCH OR DEVELOPMENT

This invention was made with government support under Grant No. EFMA-1542707 awarded by the National Science Foundation. The government has certain rights in the invention.

BACKGROUND

Interrogating the structural and dynamic properties of biomolecules has revealed much information about the roles various molecules play in living systems.

While various tools for studying DNA, RNA, and proteins are available, recent advances in nanotechnology have enabled new devices that allow single molecule probing. Among these tools, the nanopore allows the electrical detection of the properties of individual unlabeled molecules at high throughput (1-4). Nanopores can probe entities as small as hydrogen isotopes (5) and as large as viruses and cells (6). Various features of macromolecules have been probed at the molecular level, including the stability of duplex DNA molecules (7), secondary structure in RNA molecules (8,9), and the sequence of DNA (10) and RNA (11) molecules.

The principle of nanopore sensing involves the application of a voltage across a membrane separating two chambers, each containing an electrolyte solution. The nanopore forms the sole fluidic connection between the chambers. This produces a steady state ion current across the pore, also resulting in a highly localized electric field in the pore. The field, which protrudes outside the pore confines, draws charged molecules into and through the nanopore. During this process, the ion flux is impeded, resulting in a distinct electrical signature that represents the molecular occlusion of the pore. Various experimental parameters can influence the signal in a nanopore-based study, including the pore geometry (12), applied voltage (force) (13), electrolyte ionic strength (14), and hydrostatic pressure (15). In addition to these, temperature is an important parameter that can affect molecular transport kinetics, molecular structure, and molecular stability.

A common method to control temperature in a nanopore is to enclose the nanopore cell in a heating/cooling chamber (16). However, this method is slow and subjects all of the molecules in the bath to the same temperature, regardless of whether they are interrogated in the nanopore or not. More elegant versions of experiments with temperature as a variable involve local and rapid heating of some interrogation volume that contains a molecule of interest. For example, FRET-based thermal studies on single DNA molecules have been reported, in which a pulsed IR beam was used to locally induce temperature changes and a coincident visible laser was used to probe the FRET signal (17). Also, plasmonic enhancement of temperature has been demonstrated to rapidly affect temperatures locally, having been used, for example, for killing target cells (18). A protein nanopore was chemically conjugated to a plasmonic system that consisted of several gold nanoparticles, and optical control over temperature around the nanopore was demonstrated by showing enhanced ionic current through the pore (19). In this system, light absorption excites plasmonic oscillations in the gold nanoparticles, which heats the nearby electrolyte solution. This in turn reduces the electrolyte viscosity and increases ion mobility, measured as an increased ion current through the pore. In another system, DNA melting was probed using a biological pore heated with an IR-based direct absorption heating of the aqueous medium (20), with >100 ms required to achieve thermal steady state. A more complicated approach involved infrared laser irradiation of a plasmonic bowtie structure around the pore to achieve temperature control (21-25).

There remains a need for methods and systems to provide rapid heating of selected nanoscale environments.

SUMMARY

The present technology provides an apparatus and method for producing a local optothermal effect that can be used to selectively apply heat to a nanoscale environment in a controlled manner. In certain embodiments, the apparatus is capable of rapidly scanning the temperature of a nanoscale object such as a molecule or biomolecular complex and to interrogate properties of that object at high throughput. The optothermal effect can be used to provide essentially instantaneous heating, within microseconds, in a nanoscale environment.

The technology utilizes laser irradiation of a solid state material to heat a nanoscale point of interest, such as the tip of an atomic force microscope (AFM), a flat or corrugated surface, or a nanopore. The laser beam excites the solid-state layer that is in proximity to the point of interest, which then produces controlled heating through non-radiative energy transfer. The present technology achieves rapid heating of a nanoscale environment without the use of infrared irradiation or plasmonic effects.

One aspect of the technology is a device for selective heating of a nanoscale environment. The device includes a solid state material in contact with the nanoscale environment, a laser having an emission wavelength falling within an absorption band of the solid state material, and one or more optical elements for focusing light from the laser selectively on the nanoscale environment. Irradiation of the solid state material with the laser results in selective heating of the nanoscale environment by the solid state material.

Another aspect of the technology is a method of selectively heating a nanoscale environment. The method includes the steps of: (a) providing the device described above; and (b) irradiating the solid state material with light from the laser, whereby the light is absorbed by the solid state material and the nanoscale environment is selectively heated.

Still another aspect of the technology is a temperature controlled single molecule nucleic acid sequencing system including the device described above.

Yet another aspect of the technology is a temperature controlled atomic force microscope (AFM) including the device described above, wherein the laser is aligned with the axis of the AFM probe.

Even another aspect of the technology is a temperature controlled single molecule bioreactor system including the device described above.

The technology can be further summarized in the following listing of embodiments.

1. A device for selective heating of a nanoscale environment, the device comprising:
   a solid state material in contact with the nanoscale environment;
   a laser having an emission wavelength falling within an absorption band of the solid state material; and
   one or more optical elements for focusing light from the laser selectively on the nanoscale environment;
   wherein irradiation of the solid state material with the laser results in selective heating of the nanoscale environment by the solid state material.
2. The device of embodiment 1, wherein the solid state material comprises silicon nitride and the laser emits light at 532 nm.
3. The device of embodiment 1 or 2, wherein the solid state material encloses or partially encloses the nanoscale environment.
4. The device of any of the preceding embodiments, wherein the solid state material is configured as a substrate supporting the nanoscale environment, as one or more walls of a chamber contacting the nanoscale environment, as a probe extending into the nanoscale environment, or as a coating of said substrate, said one or more walls, or said probe.
5. The device of any of the preceding embodiments, wherein the nanoscale environment has a volume in the range from about 1 $nm^3$ to about $10^9$ $nm^3$.
6. The device of any of the preceding embodiments, wherein the nanoscale environment is aqueous.
7. The device of any of the preceding embodiments, further comprising an acousto-optical modulator or an electro-optical modulator that controls the output power of the laser.
8. The device of any of the preceding embodiments, wherein the one or more optical elements are provided by a microscope objective.
9. The device of any of the preceding embodiments that is capable of heating said nanoscale environment by about 10° C. to about 90° C. without significantly heating another nanoscale environment that is about 15 µm distant from said nanoscale environment.
10. The device of any of the preceding embodiments that is configured for heating a nanoscale environment containing a single molecule.
11. The device of any of the preceding embodiments, wherein the solid state material is configured as an ultrathin sheet and the nanoscale environment comprises a nanopore disposed in said sheet.
12. The device of embodiment 11 further comprising two compartments on either side of said sheet, the compartments coupled by said nanopore, at least one of said compartments comprising a transparent window for illumination of the nanopore by the laser.
13. The device of embodiment 12, further comprising a microscope, wherein an objective of the microscope provides the one or more optical elements.
14. The device of embodiment 13, wherein the microscope is equipped for fluorescence spectroscopy and/or fluorescence imaging.
15. The device of embodiment 12, further comprising an electrode disposed in each of said compartments, a voltage clamp amplifier for controlling the voltage between the two electrodes and measuring current flow between the electrodes, and a computer programmed for recording, processing, and analyzing the measured current.
16. The device of any of the preceding embodiments, further comprising one or more additional nanoscale environments, wherein the device is configured for heating the nanoscale environment and one or more additional nanoscale environments either sequentially or simultaneously.
17. The device of embodiment 16, wherein the device comprises a plurality of chambers, each comprising a single nanopore disposed in an ultrathin sheet of said solid state material.
18. A method of selectively heating a nanoscale environment, the method comprising the steps of:
   (a) providing the device of any of the preceding embodiments;
   (b) irradiating the solid state material with light from the laser, whereby the light is absorbed by the solid state material and the nanoscale environment is selectively heated.
19. The method of embodiment 18, wherein the nanoscale environment is heated by about 10° C. to about 90° C.
20. The method of embodiment 19, wherein the heating extends over a volume from about 1 $nm^3$ to about $10^9$ $nm^3$.
21. The method of any of embodiments 18-20, wherein the nanoscale environment contains an object that is heated.
22. The method of embodiment 21, wherein the object is a molecule, a macromolecular complex, a nanoparticle, a virus, or a cell.
23. The method of embodiment 22, wherein a single molecule is heated, and the molecule is a nucleic acid, protein, enzyme, nucleic acid polymerase, or DNA origami structure.
24. The method of embodiment 23, wherein the molecule is a nucleic acid and the method further comprises carrying out a single molecule PCR reaction using the nucleic acid molecule.
25. The method of any of embodiments 18-24, further comprising monitoring the temperature of the nanoscale environment.
26. The method of embodiment 25, wherein the nanoscale environment comprises a nanopore and temperature is monitored by measuring conductance through the nanopore.
27. The method of any of embodiments 18-26, wherein the nanoscale environment is heated essentially instantaneously.
28. The method of embodiment 27, wherein heating to a new steady state temperature occurs within less than 10 microseconds after starting the laser illumination of the steady state material.
29. The method of embodiment 28, wherein heating to a new steady state temperature occurs within less than 1 microsecond after starting the laser illumination of the steady state material.
30. The method of any of embodiments 18-29, wherein heating of the nanoscale environment is by a non-radiative energy transfer from the solid state material to the nanoscale environment.
31. The method of any of embodiments 18-30, wherein an object is trapped within the nanoscale environment by electrophoresis, pressure-driven fluid flow, electroosmosis, thermophoresis, or a combination thereof.
32. The method of any of embodiments 18-31, wherein a structural rearrangement, folding, or unfolding of a molecule in the nanoscale environment is determined.
33. The method of embodiment 32, wherein a conformational change of a molecule in the nanoscale environment is determined using fluorescence resonance energy transfer (FRET).

34. The method of any of embodiments 18-33, wherein the intensity of laser illumination is modulated, resulting in modulation of temperature of the nanoscale environment.

35. The method of embodiment 34, wherein the solid state material is irradiated using a ramp of increasing later intensity and results in a ramp of increasing temperature of the nanoscale environment.

36. The method of embodiment 34, wherein a melting temperature of a nucleic acid molecule in the nanoscale environment is determined.

37. The method of any of embodiments 18-36, wherein step (b) is repeated so as to separately heat two or more different nanoscale environments.

38. The method of any of embodiments 18-37, wherein single molecule sequencing at a nanopore is performed on one or more nucleic acid molecules at a temperature above ambient temperature.

39. The method of any of embodiments 18-38, which does not utilize infrared irradiation or a plasmonic effect.

40. A temperature controlled single molecule nucleic acid sequencing system comprising the device of any of embodiments 1-17.

41. A temperature controlled atomic force microscope (AFM) comprising the device of any of embodiments 1-17, wherein the laser is aligned with the axis of the AFM probe.

42. A temperature controlled single molecule bioreactor system comprising the device of any of embodiments 1-17.

43. A temperature-activated DNA chip fabrication system comprising the device of any of embodiments 1-17.

BRIEF DESCRIPTION OF THE DRAWINGS

FIG. 1B shows a schematic diagram of the setup. A collimated 532 nm laser beam overfills the back plane of a 60× objective lens of an inverted microscope, which is used to focus the light on a silicon nitride ($SiN_x$) solid-state membrane containing a nanopore fabricated in a pre-thinned region. A pair of electrodes is used to apply bias and measure current across the nanopore. Molecular translocation induces transient blockades in the current signal (current vs. time trace shows 500 bp DNA translocation events at V=300 mV, pore diameter=2.7 nm). The laser power is controlled using an electro-optic modulator (up to 800× attenuation, approx. 4 μs response time). FIG. 1C. Inset, right: Top-view of a back-illuminated 50 μm×50 μm freestanding 50-nm-thick silicon nitride membrane with a pattern of four 25-nm-thick circular regions (scale bar=5 μm). A 3 nm diameter pore is drilled in one of the thin regions (circle in top left quadrant, left inset is a pore TEM image). Top and bottom current traces show the impact of a 10 mW laser on the current through the nanopore (V=200 mV), switched on at the asterisk, with the laser illumination placed either on the nanopore (top trace) or off the nanopore (bottom trace, circle near center of image). FIG. 1D. Absorbance spectrum of a 200-nm-thick silicon nitride membrane (left trace) and photoluminescence spectrum (right trace) of a 50-nm-thick freestanding silicon nitride membrane excited by a 532 nm laser spot (vertical line at 532 nm). FIG. 1E. Simulation of the steady-state temperature distribution, calculated using a 2D finite-element COMSOL simulation. Simulated structure is shown in FIG. 5A. A 42.5-nm-thick silicon nitride membrane was modeled as having a 3 nm diameter nanopore through its center and surrounded by water, with nonradiative decay following a 12.5 mW laser excitation incident on the membrane.

FIG. 3A. Streaming potential measurements carried out by applying 2 s pressure steps to the cis chamber of a nanopore and recording the streaming potential, (electrolyte: 0.4 M KCl, pH 7.8 or pH 5.0). Data are shown for several different laser powers, P. Pore sizes for pH 7.8 and pH 5.0 experiments were 7.6 and 5.5 nm, respectively. FIG. 3B. Surface charge density a vs. laser power for three pores of diameters 7.6, 5.9, and 2.8 nm at pH 7.8. Shaded region represents the overall range of a values measured (mean and st. dev. indicated).

FIG. 4A. Upper curve shows measured current enhancement factors, I(P)/I(0), as a function of laser power applied to a 3 nm diameter $SiN_x$ pore with a 14.1 nm effective thickness (V=100 mV). Lower curve shows a 28 nm diameter pore with 16.5 nm thick $Al_2O_3$ and 5 nm thick $SiN_x$ (V=100 mV). The line represents a fit to a standard conductivity vs. temperature model (see eq 1), whereas the fitted curve accounts for thermophoresis (see eq 3). Inset shows I-V curves for the pore at P=0 and 12.5 mW (curve with steeper slope). The top scale is the corrected temperature obtained from the fits (note: this scale is not applicable to the $Al_2O_3$+$SiN_x$ pore due to reduced heating by the laser). FIG. 4B. First three traces from left show continuous 10 s current trace samples for a 4 nm diameter pore with a 9.7 nm effective thickness when 30 nM 1 kbp double-stranded DNA was in the cis chamber, and 200 mV was applied to the trans chamber, at different indicated pore temperatures (Tp) induced by laser heating. The right side trace was obtained using P=0 mW after collecting data at increasing laser powers (note that slight pore expansion leads to higher baseline current. FIG. 4C. Solid circles show mean capture rates as a function of pore temperature for the experiments in FIG. 4B, and open circle shows mean capture rate obtained after recooling.

FIGS. 5A-5C show the physical pore model built in COMSOL (5A), the calculated temperature profile along the pore axis for P=0-12.5 mW (5B), and calculated peak temperature (Tp) at the pore vs. laser power (5C).

FIG. 6A shows normalized ion concentration profile as a function of axial distance from the pore, and FIG. 6B shows mean fractional ion concentration in the pore as a function of laser power.

FIGS. 7A-7E show the results of an experiment to determine melting characteristics of single nucleic acid molecules using a nanopore (single molecule thermal melting). FIG. 7A shows continuous 2 s current trace samples of Arg-tRNA at different nanopore temperature (Tp) values (indicated above each respective trace) through a 3 nm diameter, 19.6 nm effective thickness pore (V=600 mV). FIG. 7B shows traces similar to those of 7A, but for a three-way DNA junction ($3WJ_{37.5}$) translocation through a 3 nm diameter pore with a 14.7 nm effective thickness at V=200 mV for different $T_p$ values. FIG. 7C shows mean log($t_d$) vs $T_p$ for $3WJ_{37.5}$ and Arg-tRNA, as well as a sigmoid fit through each data set. Based on the fit, $T^*_m$ values of 33.0 and 38.3° C. were obtained for $3WJ_{37.5}$ and Arg-tRNA, respectively. FIG. 7D shows sequences designed to form 3WJ-DNA nanoparticles with controlled $T_m$ of a branching site. The sequences of $3WJ_{30C}$ are shown above (A=SEQ ID NO:1; B=SEQ ID NO:2; C=SEQ ID NO:3), and the sequences of $3WJ_{37.5}$ are shown below (A=SEQ ID NO:4; B=SEQ ID NO:5; C=SEQ ID NO:6). Ethidium bromide total staining native-PAGE (not shown) confirmed the correct assembly of the 3WJ DNA molecules. The lower part of FIG. 7D shows a 3D model and schematic representation of melting steps for the $3WJ_{30C}$ molecule. The 3D model was built using Discovery Studio Visualizer. FIG. 7E shows mean log($t_d$) vs $T_p$ for $3WJ_{30C}$ under applied voltages of 150 mV and 300 mV using a 3 nm diameter pore with a 11.6 nm effective thickness, showing $T^*_m$ values of 27.0 and 24.7° C., respectively.

In FIG. 8A the top panels show a schematic depiction of the three steps of the single-molecule thermoscopy experiment: 1) constant voltage applied to capture an Arg-tRNA molecule; 2) capture triggers a thermal scan achieved by a linear sweep of increasing laser power; 3) molecular translocation through the pore in a melted state. FIG. 8A middle panel shows exemplary single-molecule normalized current traces obtained by Arg-tRNA thermoscopy for a 3 nm diameter pore with a 10.3 nm effective thickness, either without (No Ramp, V=350 mV) and with (Ramp, V=300 mV) thermal ramping. Capture of molecules was set to t=0 ms. FIG. 8A lower panel shows the corresponding laser ramp employed (power increased at 2.4 mW/ms). FIG. 8B shows histograms of Arg-tRNA melting times obtained for different applied voltages, and corresponding melting temperatures shown on the top axis. FIG. 8C shows mean melting temperatures, $T^*_m$, as a function of voltage. The linear fit reveals a zero-force melting point of $T_m$=63.2° C., in agreement with tRNA bulk melting data from the literature.

FIGS. 9A-9C show schematic representations of systems for selectively heating molecules of interest. FIG. 9A shows a system for laser irradiation of an AFM tip which can be used to heat a molecule on a substrate, such as a protein. FIG. 9B shows a system for replicating a single DNA molecule, such as by single molecule PCR. FIG. 9C shows a process for fabricating a DNA chip using selective laser-induced heating of a silicon nitride substrate and resulting in sub-micron areas (spots) having known DNA sequences.

DETAILED DESCRIPTION

The present technology makes use of a photothermal effect in which a visible laser irradiant on a solid state material capable of absorbing the laser radiation, such as silicon nitride, causes nonradiative heating. This results in a nearly instantaneous, highly localized, nanoscale thermal gradient around the solid state material. Depending on the laser power applied, the effect can heat the surrounding environment from ambient temperature to near the boiling point of water. This optothermal effect is the basis for methods, and devices and systems configured to carry out the methods, useful to heat and/or thermoregulate a nanoscale environment for purposes of characterizing the structure and function of single molecules, such as biomolecules, molecular complexes, nanoparticles, nanostructures, nanocircuits, viruses, and cells, as well as to replicate or fabricate such nanoscale or even microscale objects or portions thereof.

Figure 1A:
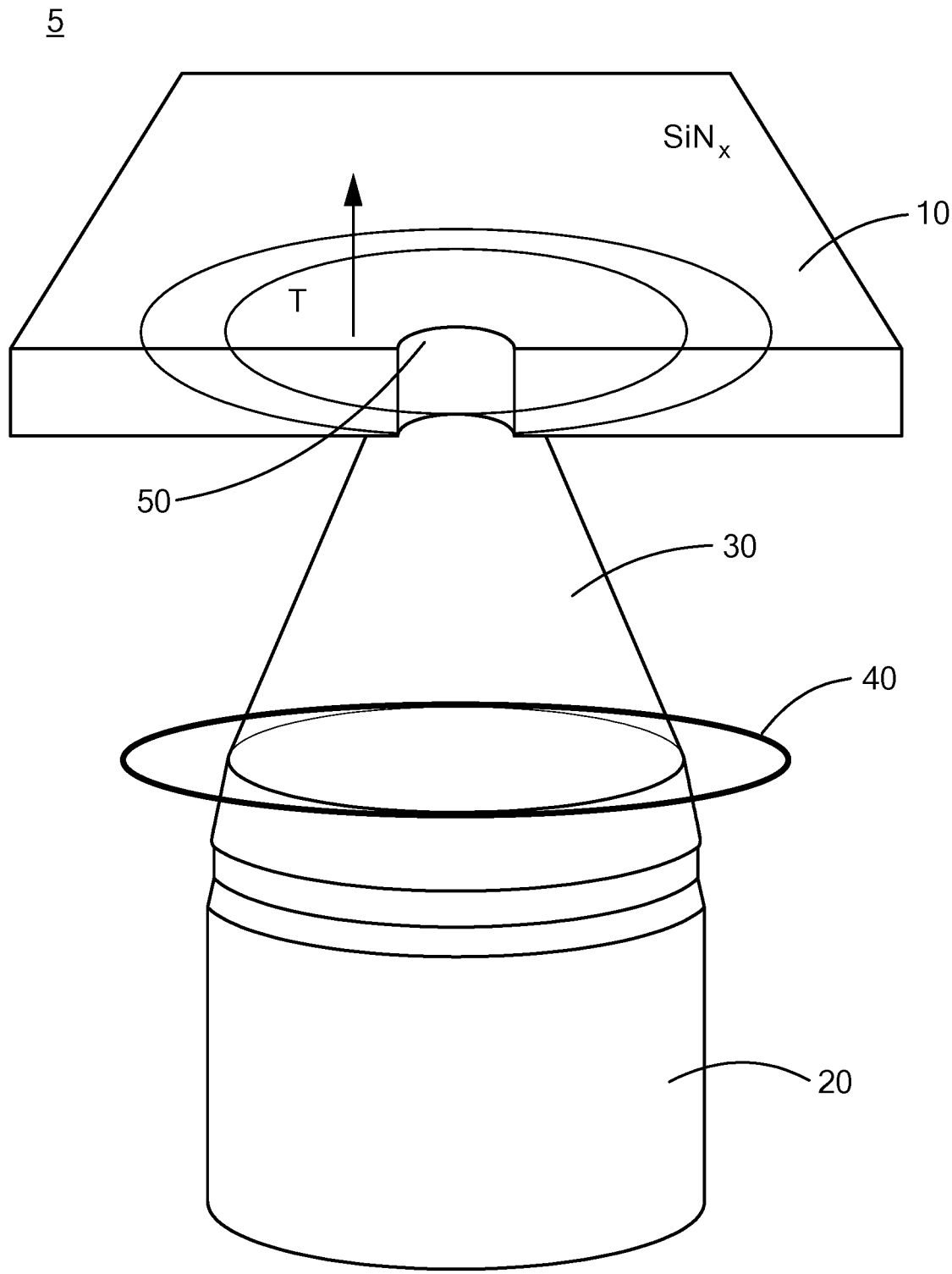
FIG. 1A shows a schematic representation of device 5 for heating a nanoscale environment. Ultrathin membrane 10 formed of a solid state material (silicon nitride in this embodiment) is irradiated with light 30 from laser 20 after passing through optical element 40 which focuses the light on nanoscale environment 50. Light 30 has a wavelength that is absorbed by the solid state material, resulting in heating of the nanoscale environment by non-radiative energy transfer. In this embodiment, the solid state material contains a nanopore; however, in alternative embodiments, the solid state material can be a featureless or structured substrate having any desired form, such as a planar substrate to support molecules of interest, or the solid state material can be the tip of an AFM probe, a nanoparticle, or a nanostructure.

A device and method of the present technology are exemplified schematically in FIG. 1A. Nanooptical heating device 5 includes solid state material 10 which is irradiated by laser 20 with light 30, which is focused by optical element 40 to illuminate nanoscale environment 50 which is in contact with the solid state material. Without intending to limit the invention to a particular mechanism, it is believed that absorption of the emitted laser light by the solid state material results in non-radiative energy transfer to the immediate environment of the solid state material, which becomes rapidly heated. The degree of heating depends on the intensity of the laser emission and therefore depends on the power of the laser.

The solid state material can include or consist of any solid state material capable of absorbing laser light and non-radiatively emitting energy in response thereto to the immediate environment of the material. Preferably the solid state material is also capable of use in fabrication of nanoscale structures, for the better definition of the heated nanoscale environment and use of the highly localized heating effect. A preferred solid state material is silicon nitride ($SiN_x$), including SiN, $Si_2N$, $Si_2N_3$, and $Si_3N_4$. Other solid state materials that could be used include GaS, GaSe, InS, InSe, $HfS_2$, $HfO_2$, $HfSe_2$, $HfTe_2$, $MoS_2$, $MoSe_2$, $MoTe_2$, $NbS_2$, $NbSe_2$, $NbTe_2$, $NiS_2$, $NiSe_2$, $NiTe_2$, $PdS_2$, $PdSe_2$, $PdTe_2$, $PtS_2$, $PtSe_2$, $PtTe_2$, $ReS_2$, $ReSe_2$, $ReTe_2$, $TaS_2$, $TaSe_2$, $TaTe_2$, $TiS_2$, $TiSe_2$, $TiTe_2$, $WS_2$, $WSe_2$, $WTe_2$, $ZrS_2$, $ZrSe_2$, and $ZrTe_2$. The solid state material can have any form, shape, and dimensions preferred according to its use. For example, it can be in the form of a planar substrate, a thin film, ultrathin film, or coating, a nanoparticle, an AFM probe tip, or a structural component of a circuit, such as a microcircuit or nanocircuit, or a microelectromechanical device or nanoelectromechanical device. For applications requiring the use of a material that does not absorb the laser energy and provide non-radiative heating, the material can be coated with a layer of a suitable laser light-absorbing solid state material such as silicon nitride. The solid state material preferably is not suitable for plasmonic effects when irradiated by the laser. In a preferred embodiment, the solid state material is in the form of an ultrathin membrane, having a thickness in the range of 5 nm to 100 nm and containing a nanopore having a diameter in the range from 2 nm to 20 nm, which is useful for interrogating macromolecules that transit through the pore and induce changes in ionic currents flowing through the pore.

The choice of laser will usually be dictated by the choice of solid state material and its absorbance spectrum. The absorption spectrum of silicon nitride is characterized by a single broad peak centered at about 570 nm; thus, a commonly available green laser having an emission at 532 nm is well suited for absorbance by silicon nitride. The 532 nm wavelength is generally not well absorbed by water or most biomolecules, making it selective for silicon nitride when used with aqueous buffers and biological systems. Visible light lasers are preferred. The laser light should not be in the infrared range, because that would result in the direct heating of irradiated structures, which is not contemplated in the present technology.

The laser light should preferably illuminate a small area of the solid state material, and therefore it is necessary to focus the light emitted by the laser using an optical system containing one or more optical elements, such as lenses. A high power microscope objective, such as a 40×, 50×, 60×, or 100× objective, is suitable; however, any optical system capable of focusing the laser beam onto the solid state material near to the nanoscale environment of interest can be used. The power of the laser is preferably modulated on a microsecond time scale using either an electro-optic modulator or an acousto-optic modulator.

With the present technology, a nanoscale environment is heated selectively. The nanoscale environment can have an extent or dimension in the range from 1 nm to 999 nm, and can encompass a volume of space from about 1 $nm^3$ to about $10^9$ $nm^3$. Preferably, the nanoscale environment encompasses a volume less than $10^9$ $nm^3$, such as less than $10^6$ $nm^3$, less than $10^5$ $nm^3$, less than $10^4$ $nm^3$, less than $10^3$ $nm^3$, or less than 100 $nm^3$. The selectivity of the heating effect for the chosen nanoscale environment is such that the heating effect is highly localized, and rapidly attenuates with increasing distance from the locus of laser illumination. For example, the heating effect preferably attenuates to less than 10%, less than 5%, or less than 1% of its maximum at a distance from the locus of illumination of about 10 nm, 20 nm, 50 nm, 100 nm, 200 nm, 300 nm, 500 nm, or 1000 nm. With the present technology, the nanoscale environment is heated rapidly, achieving a steady state temperature or temperature profile upon steady state laser illumination within 100 microseconds, or within 20 microseconds, or essentially instantaneously, such as within 10 microseconds, or within 5 microseconds, or within 1 microsecond of the initiation of steady state laser illumination.

The methods and devices of the present technology can be used in various ways. They are useful, for example, to probe or characterize molecules or molecular structures or complexes, particularly including biomolecules, polymers, biopolymers, nucleic acids, DNA, RNA, proteins, enzymes, polysaccharides, biomolecular complexes, micelles, nanoparticles, nanoelements, and nanostructures, whether naturally occurring or synthetic. The form of the solid state material can be selected to function according to the type of molecule or structure to be probed. For example, an ultrathin solid state membrane containing a nanopore can be used to investigate the sequence, secondary structure, folding, unfolding, refolding, 3D conformation, or dimensions of a biomolecule or biopolymer, such as a nucleic acid, protein, polymer, or micelle or other lipidic structure, by measuring the blocking effect of the structure on an ionic current through the nanopore. When an AFM probe (e.g., containing $SiN_x$), is heated using a suitable laser, mounted so that the laser beam is coaxial with the probe and moves with the probe, then the probe can be used to heat individual molecules or structures that it touching to investigate heat-driven conformational changes and the like. This use is depicted in FIG. 9A, which show in the insert a simulation of a temperature profile of an irradiated tip; the form of the tip concentrates the heating effect at the tip, where it can be used to heat selected areas or components, such as a protein molecule.

Methods and devices of the present technology also can be used to actively drive biochemical or chemical reactions, or physical phase changes, in selected nanoscale embodiments or objects found within them. For example, irradiation of a selected spot on a suitable substrate can heat the substrate to drive local chemical or biochemical reactions. Given the local nature of the effect, a system using the optothermal effect of the present technology can be used to drive a selected sequence of reactions, such as enzyme reactions or protein-protein or protein-nucleic acid interactions, or to denature hybridized nucleic acids, at selected locations of a bioreactor chip, as a way of carrying out a selected sequence, such as a complex sequence, of reactions that might otherwise be impractical to carry out. Biochemical reactions or binding interactions within a single living cell also can be modulated selectively using localized application of heat to speed up selective reactions or interactions. An example of this approach is depicted in FIG. 9B, which shows how a single molecule PCR reaction can be carried out in a system containing a complex mixture of nucleic acids. The thermosensitivity of certain DNA polymerases typically used in PCR can be put to good use, in that DNA replication will not take place except when individual DNA polymerase enzymes are activated by local heating. Local heating of a nanopore also can be used to speed up single molecule nucleic acid sequencing carried out at the pore. The selectivity afforded by the nanoscale size of the laser spot makes it possible to speed up selected chemical reactions or sequencing of individual nucleic acids without affecting other molecular species in the same solution or sample.

Figure 9C:
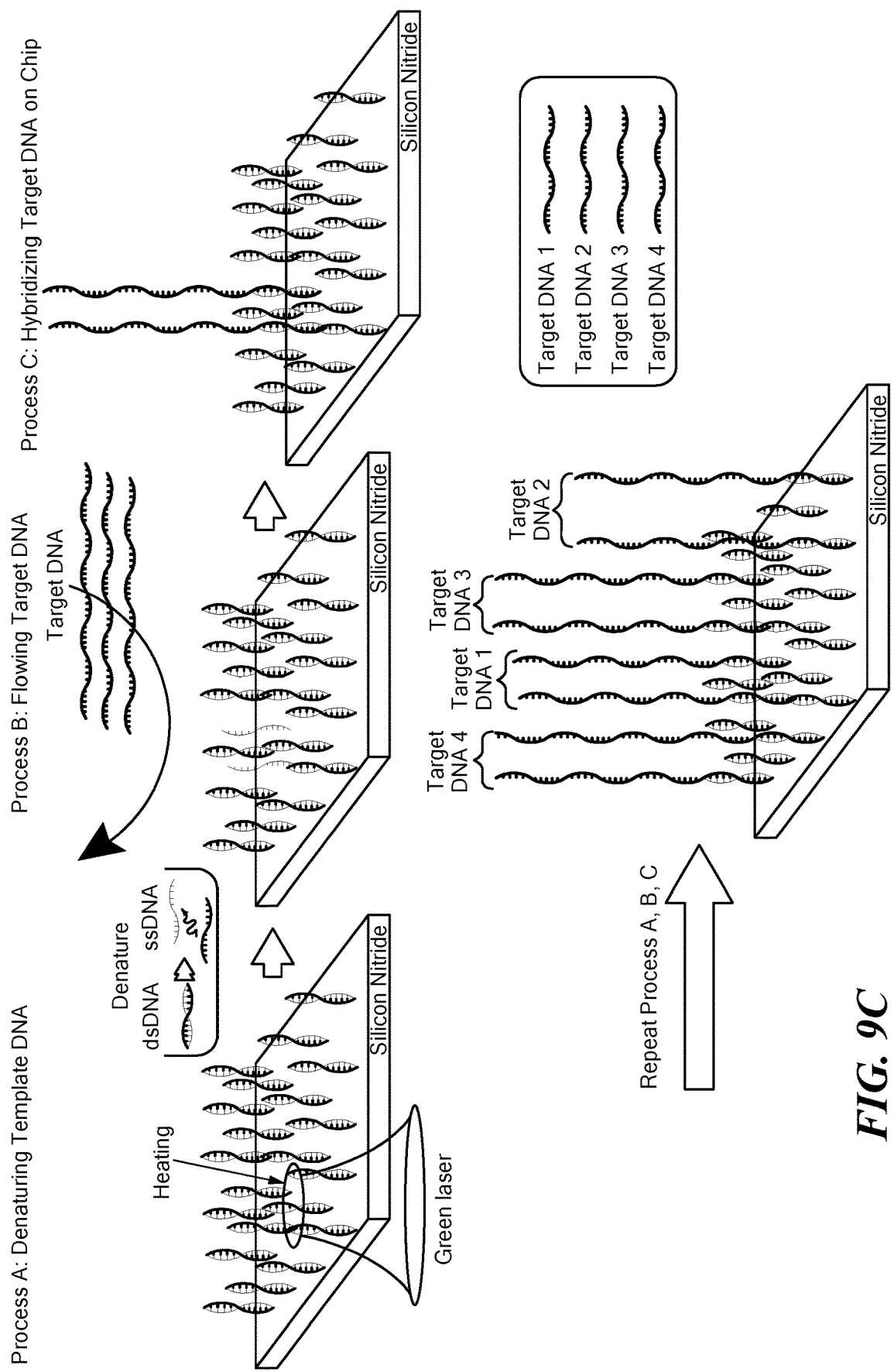

The present technology also can be used to fabricate a high density DNA chip fabrication system, as shown in FIG. 9C. A chip substrate containing a silicon nitride film on glass or quartz is initially coated with a carpet of identical or nonidentical double-stranded DNA molecules with a known sequence, chemically grafted onto the SiN membrane using established organosilane chemistry or another chemistry. In Process A, local heating of an approximately 500 nm×500 nm spot using a focused visible laser is used to melt the DNA locally, so that a single-stranded DNA forms selectively at that region. In Process B, target DNA 1, which has a section complementary to the attached DNA oligonucleotides, is flowed onto the chip such that it binds to the single-stranded region. After washing out the unbound DNA, the structure shown in Process C is obtained. If the same processes A, B, and C are repeated at different regions using a different DNA sequence for each region, a DNA chip results that contains individual spots of probe DNA having sub-micrometer dimensions. Such a chip can be read by a fluorescence microscope, resulting in a DNA chip reading system of maximally high density.

The present technology provides a photothermal effect in which a visible laser irradiant on a silicon nitride nanopore or other structure containing silicon nitride causes nonradiative heating. This results in a highly localized thermal gradient around the pore or other structure that, depending on the laser power applied, can heat the surrounding environment to in increments from about 10° C. to at least 90° C., or near boiling, or to any desired temperature in between. Calibration of the temperature achieved can be performed using ion currents for a nanopore, or using denaturation of nucleic acids with known denaturation temperatures in the absence of a nanopore.

The following examples demonstrate how the ion-current enhancement profile of a nanopore, in addition to DNA capture by the pore, and single-molecule melting of DNA and RNA molecules can be investigated and measured using the present technology.

EXAMPLES

Example 1. Nanopore Fabrication and Nanopore-Based Measurements

Nanopores were fabricated through freestanding, approximately 50 nm thick $SiN_x$ membranes, 20-50 μm in planar dimensions, which were supported by a 5×5 mm Si chip. The 50 nm thick $SiN_x$ layer was deposited using low-pressure chemical vapor deposition on a 500-μm-thick (100) oriented Si wafer that had been thermally oxidized prior to deposition to provide a 2.5-μm-thick $SiO_2$ barrier layer to reduce electrical capacitance noise. Thin regions were patterned as optical markers as previously described (34) using lithography on the membrane side followed by reactive ion etching (RIE). For complete fabrication details see ref. 44.

To fabricate a freestanding $Al_2O_3$ film with a $SiN_x$ membrane, 150 cycles of atomic layer deposition was employed to deposit 16.5 nm $Al_2O_3$ on the membrane side. After $Al_2O_3$ deposition, 25 nm thick $SiN_x$ was etched by 32 s RIE. The deposition rate of $Al_2O_3$ on $SiN_x$ and the etching rate was 0.11 nm/cycle and 0.75 nm/s. A transmission electron microscope (JEOL 2010F) was then used to drill a 2-8 nm pore through the $SiN_x$ membrane. Prior to an experiment, nanopores were cleaned using freshly heated piranha solution (1:2 mixture of $H_2O_2$ and $H_2SO_4$) for 10-15 min. Nanopore chips were then assembled in a custom PTFE cell, and an Ag/AgCl electrode was inserted into each chamber. Unless otherwise stated, the electrolyte used for experiments contained 0.4 M KCl, 10 mM Tris, and 1 mM EDTA, adjusted to pH 7.9. All pore diameters and effective thickness for measuring melting temperature in the paper were estimated from open current and ion current blockade of dsDNA translocation (34). The effective thickness was typically one-third of the total membrane thickness.

Arg-tRNA from S. cerevisiae was obtained from Barry Cooperman, UPenn. The DNA sequences (see FIG. 7D) used to assemble the three-way junctions were designed manually. The correct assemblies were initially confirmed with NUPACK.45. All DNA oligos were purchased from IDT (idtdna.com) and were gel-purified (8 M urea, 15% acrylamide). DNA strands were eluted from gel pieces using 1×TBE buffer with 0.3 M NaCl. Following precipitation in 2.5 volumes of 100% ethanol, DNA in the buffer was washed in 90% ethanol, vacuum-dried, and resuspended in doubly deionized water. To assemble the three-way junctions (3WJ), three DNA strands were mixed in equimolar concentration (1 μM final) and heated to 95° C. for 2 min. After cooling to room temperature, the constructed 3WJ-DNA buffers were adjusted to 0.4 M KCl. Concentrations of Arg-tRNA and 3WJ-DNA samples in experiments were 450 μg/μL and 20 nM, respectively.

Figure 4A:
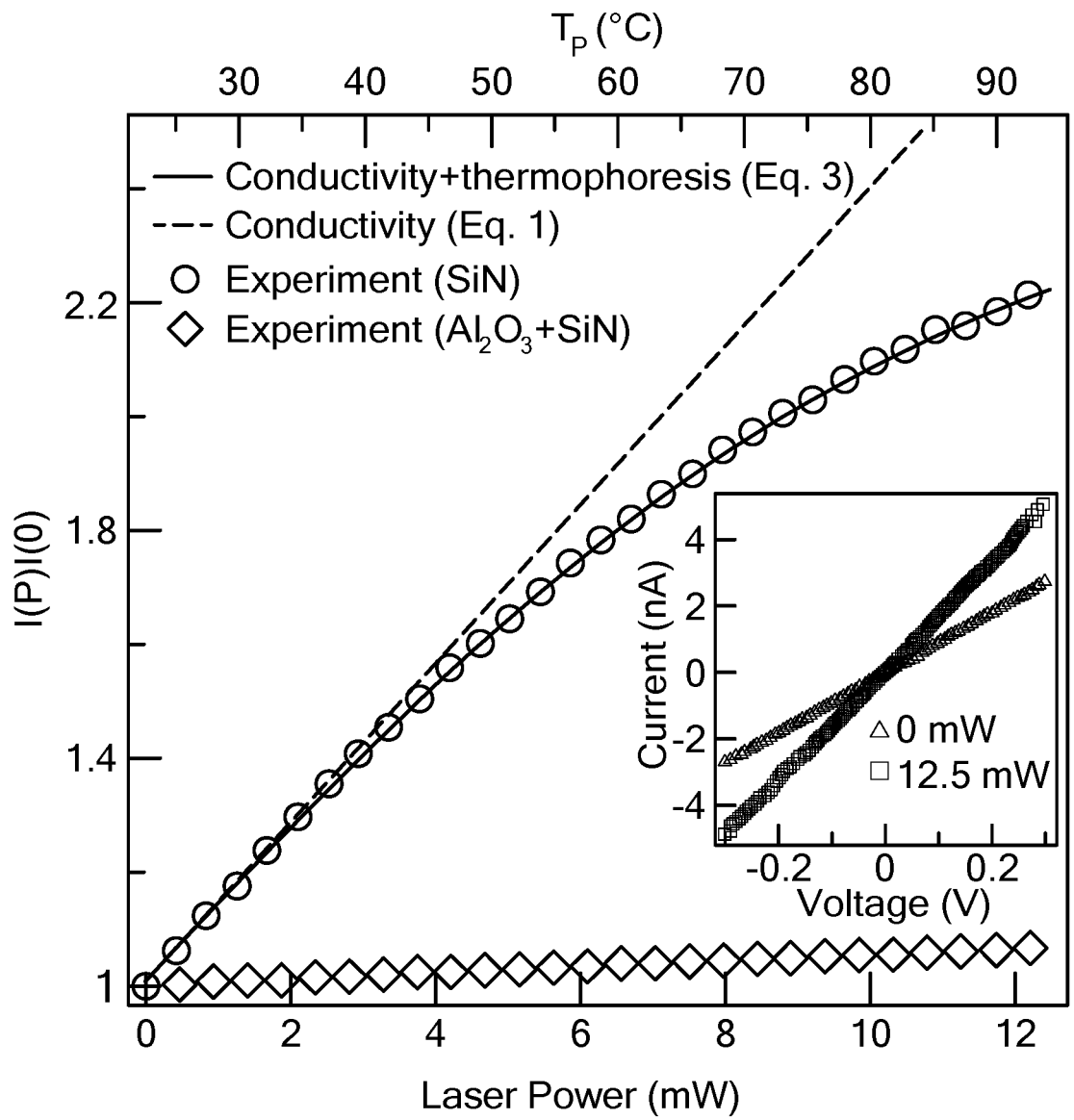
FIGS. 4A-4C show the results of a pore thermometry experiment based on ion-current enhancement data.
Figure 7A:
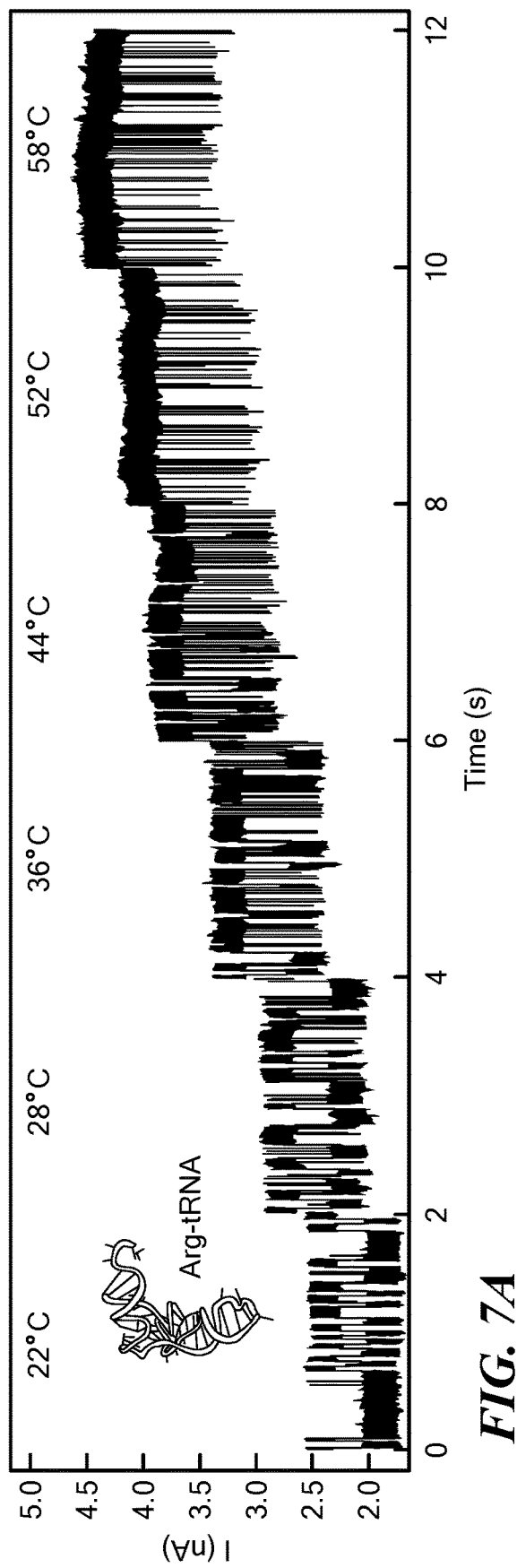
Figure 7B:
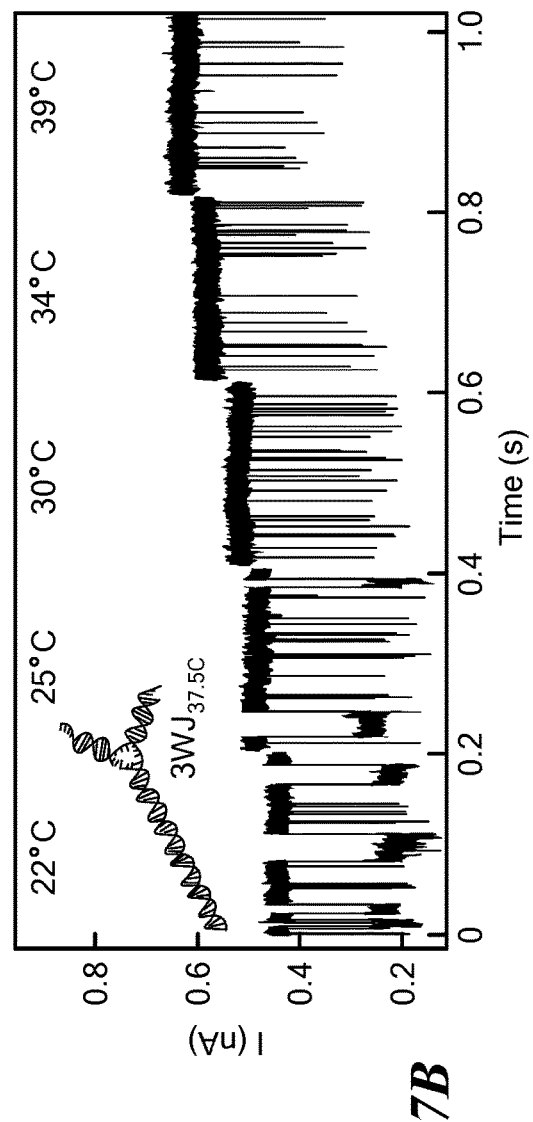
Figure 7C:
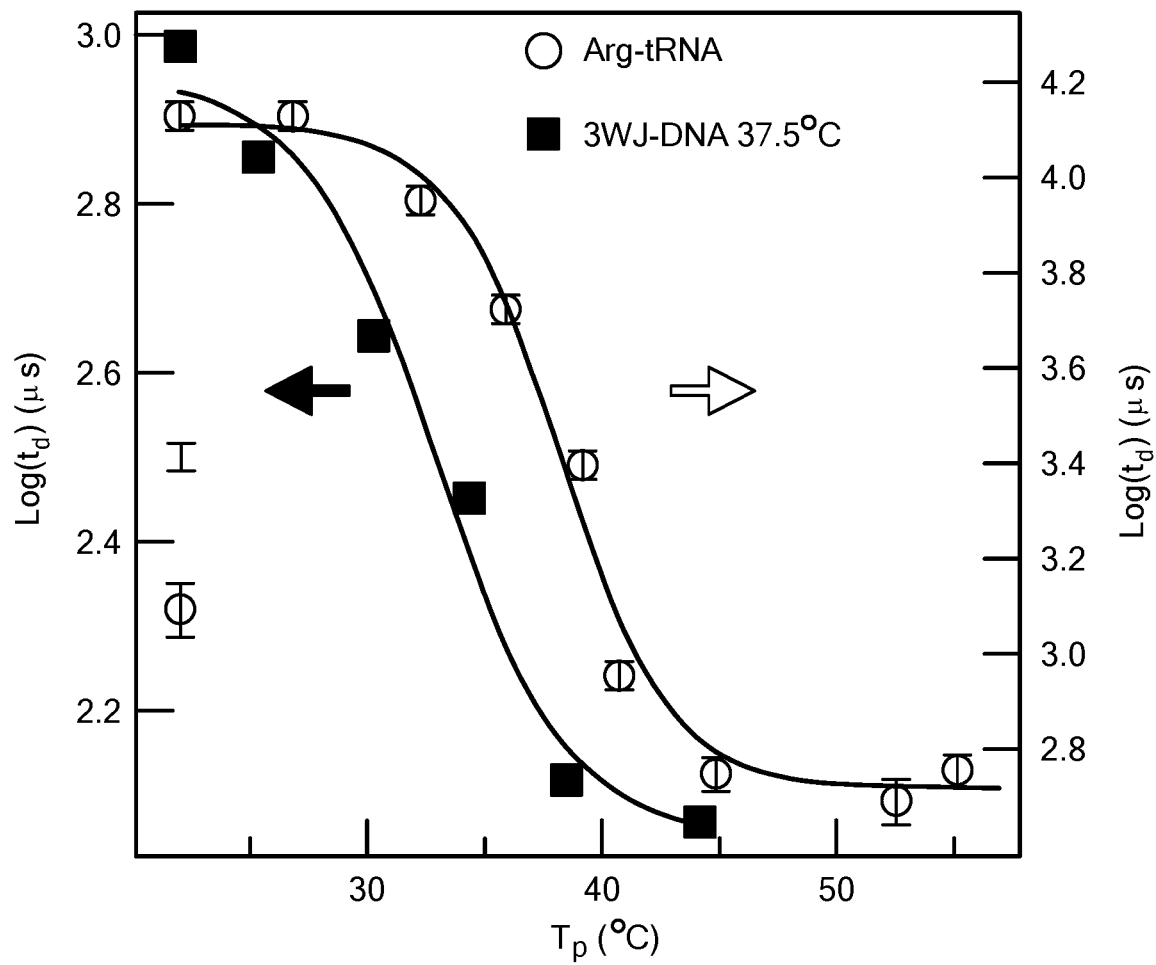
Figure 8B:
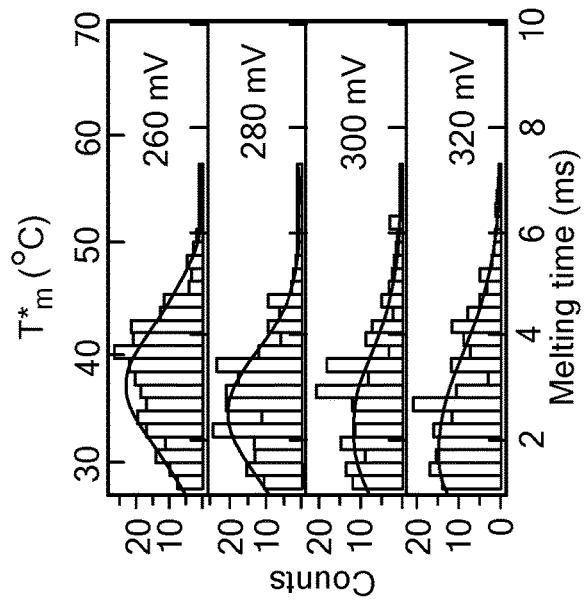
FIGS. 8A-8C show the results for single-molecule melting determination by thermoscopy.
Figure 8C:
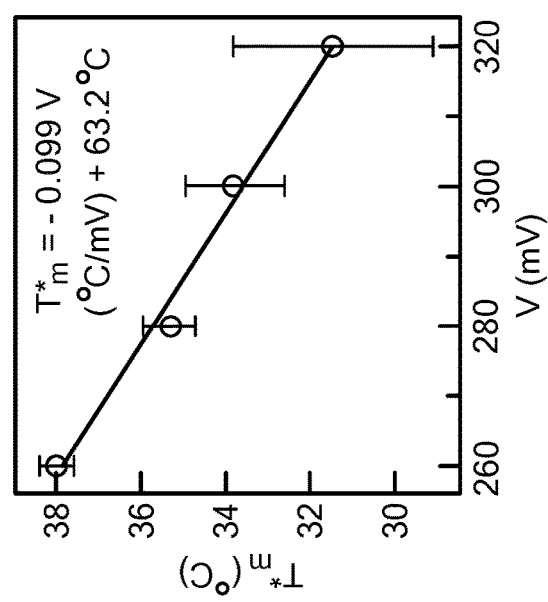
Figure 8A:
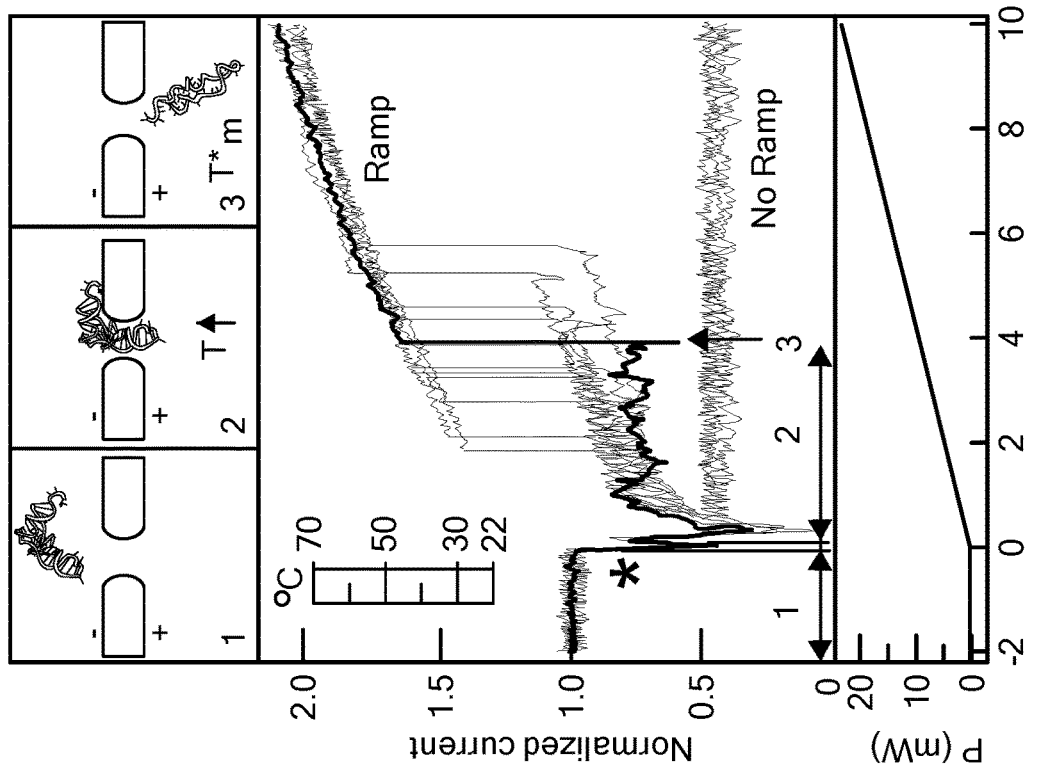

Ionic currents were recorded using an Axopatch 200B amplifier, and data were digitized at 250 kHz after filtering the current samples using the built-in Bessel filter at 100 kHz for all data except 10 kHz for data shown in FIGS. 8A-C. Further low-pass filtering prior to analysis we performed in software at 10 kHz for Arg-tRNA and 3WJ-DNA (37.5° C.) and 20 kHz for 3WJ-DNA (30° C.). Current blockades and dwell times were extracted from the current traces using custom Python software (github.com/rhenley/Pyth-Ion/). In FIGS. 7A-C, and E, and 8A-C, the temperature was calculated using I(P)/I(0) as shown in FIG. 4A.

Example 2. Apparatus for Heating a Nanopore

Figure 1B:
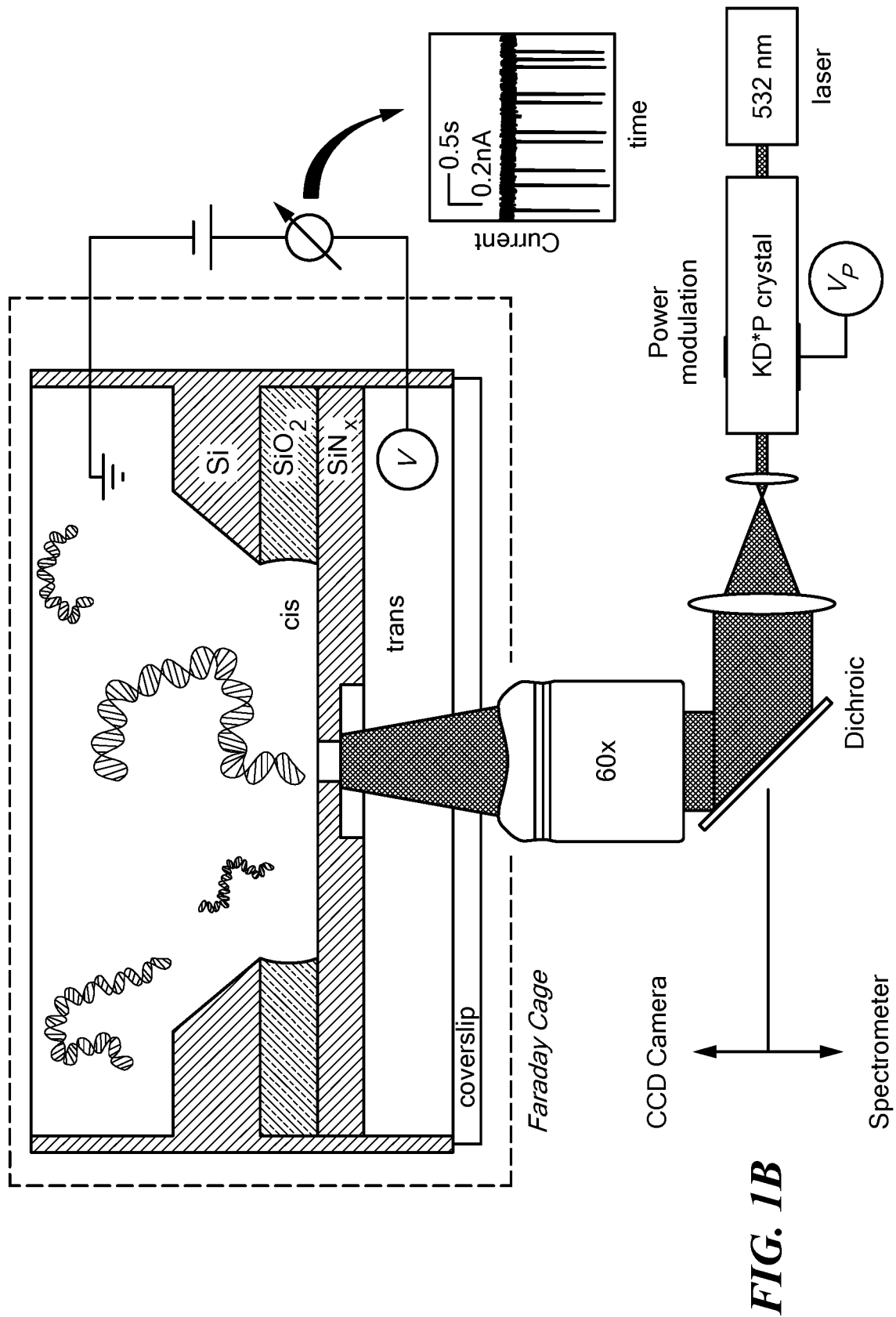
FIGS. 1B-1E show the experimental setup and results for laser-induced nanopore heating.
Figure 2:
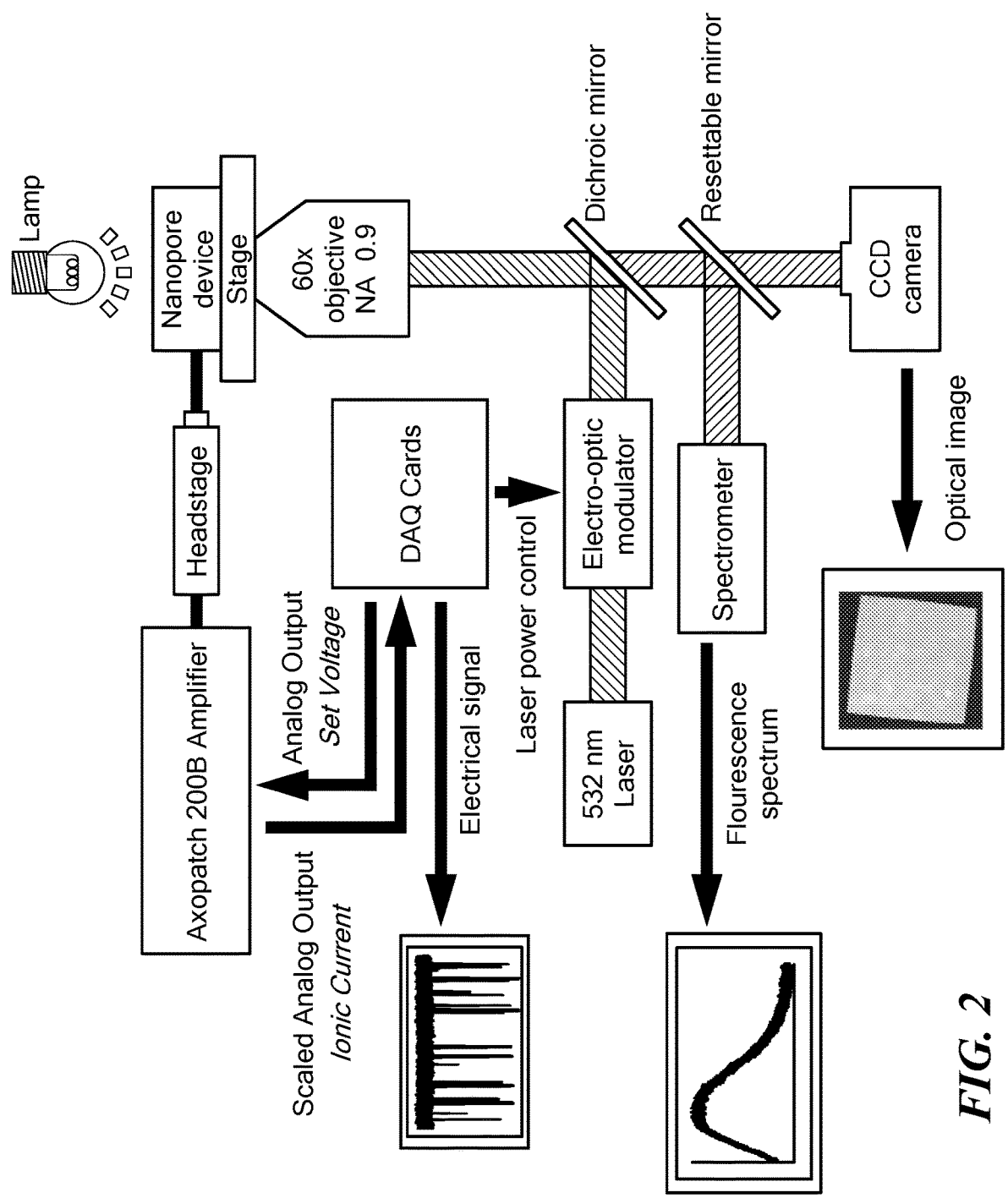
FIG. 2 is a schematic of a system for characterizing biomolecules using a nanopore cell, voltage clamp, laser, and inverted fluorescence microscope. The nanopore device was placed in a Faraday cage. A 532 nm laser (Coherent) was focused on a $SiN_x$ membrane using a N.A. 0.9, 60× air objective lens (UPlan APO, Olympus), and an XY automated stage (Applied Scientific Instrumentation) was used to control the laser position. The system was mounted atop an inverted microscope (Olympus IX71) with a manual focus objective turret. Fluorescence spectra and $SiN_x$ chip images were detected using an optical-fiber spectrometer (Thorlabs) and a CCD camera (Aihome), respectively. Laser power was controlled by an electro-optic modulator (Conoptics). An Axopatch 200B patch-clamp amplifier (Molecular Devices) was used for monitoring the electrical current and applying voltage to the nanopore. Two DAQ boards (National Instruments PCI-6230 and PCIe-6351) were used for applying voltage waveforms and digitizing the analog output current signal from the Axopatch, respectively. For thermoscopy, ion current drops, which signaled molecular capture, triggered the output of a voltage ramp to the electro-optic modulator power amplifier (M302, Conoptics), which had a fast time response (4 μs rise time).

FIG. 1B displays a schematic diagram of an apparatus for heating a nanopore (not to scale). The apparatus includes a Si chip that contains a noise-reducing $SiO_2$ layer below a free-standing $SiN_x$ membrane that contains a nanopore through the membrane. Prior to making a nanopore of 3-5 nm diameter, a periodic array of thinned $SiN_x$ circles (~2-3 μm diameter) was fabricated on the chip to serve as an optical marker for pore localization. The chip was assembled in a fluidic cell with cis and trans chambers for an aqueous electrolyte. The bottom of the cell is a glass coverslip that allows optical interrogation using an inverted microscope. An electrode (Ag/AgCl) was placed in each chamber, and the electrodes were used to apply a voltage across the membrane, leading to a steady-state current measured using a patch clamp amplifier. When a sample of macromolecules is placed in the cis chamber and voltage is applied, the passage of these molecules through the pore is indicated by transient current blockade events, visible as downward deflections from the baseline (see inset at right). A more detailed diagram of the apparatus is presented in FIG. 2.

Figure 1C:
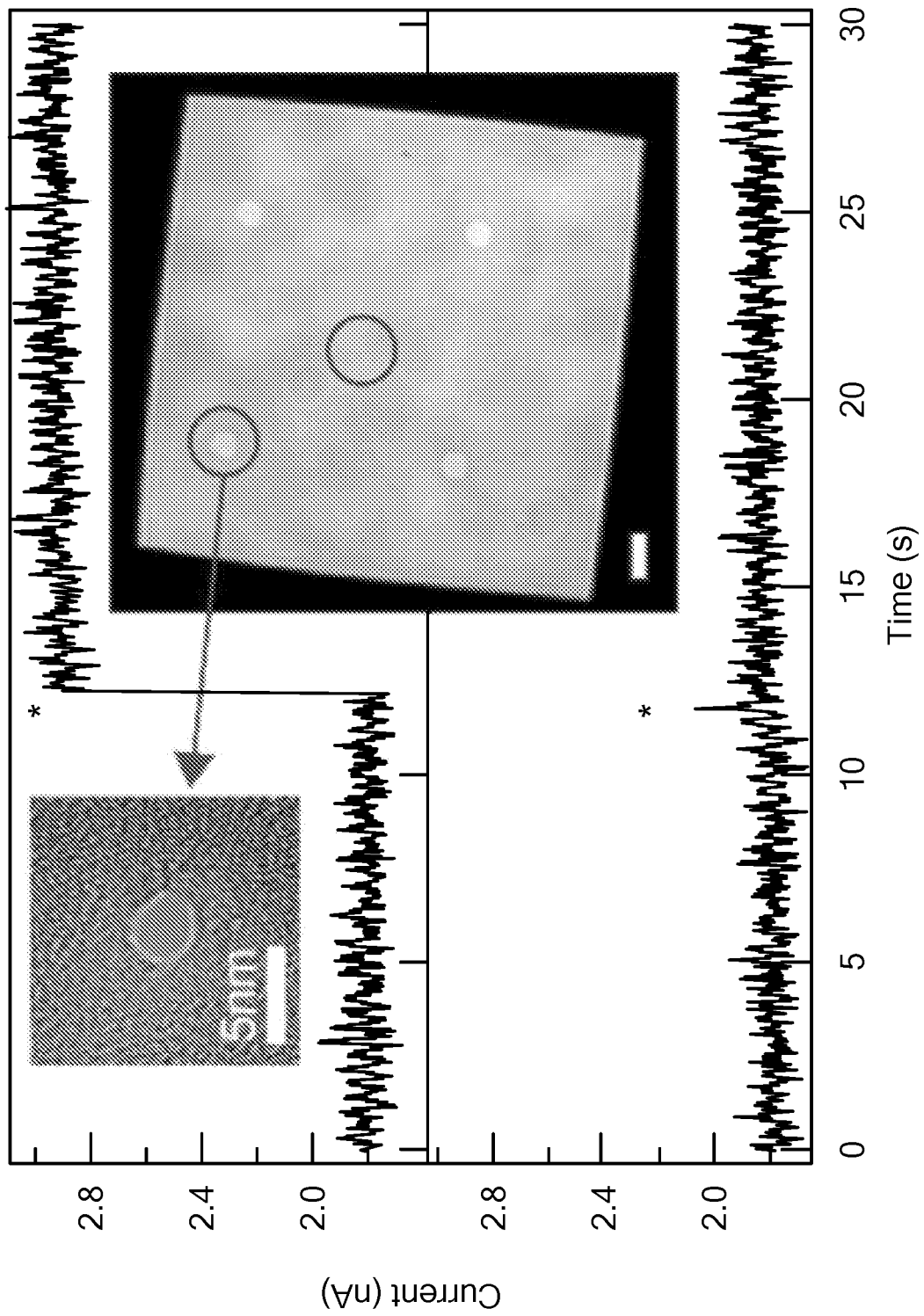
Figure 1D:
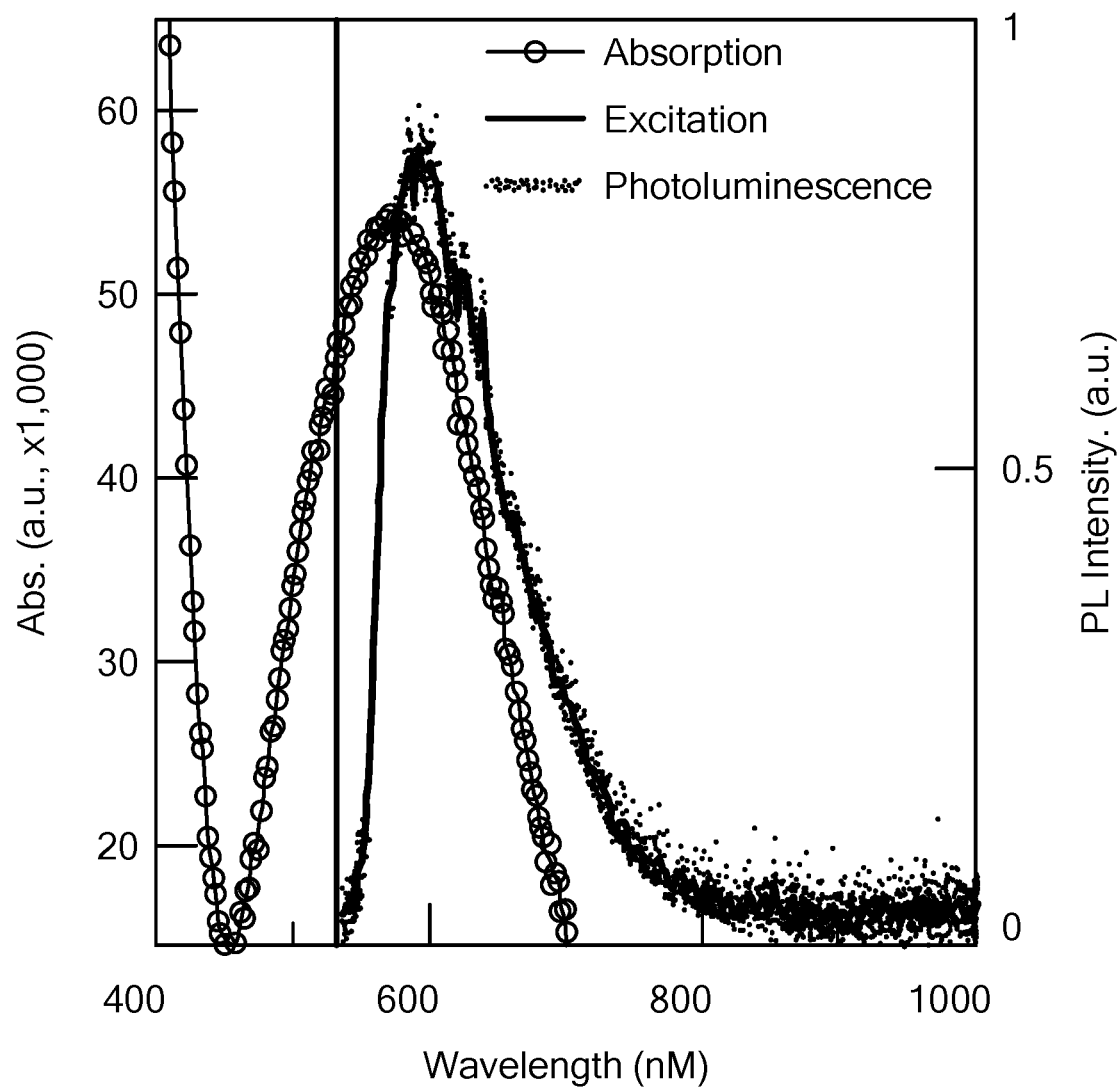

FIG. 1C shows the impact of laser irradiation on the ion current through the pore. Applying voltage (V=200 mV) across the pore and switching on the laser, focused on the pore (circle in upper left quadrant), from 0 to 10 mW (upper trace, laser on at asterisk), resulted in an instantaneous enhancement of the ion current. In contrast, when the beam was focused on the membrane at a position about 15 μm away from the pore (circle near center), there is nearly no enhancement in the ion current (lower trace). FIG. 1D shows the absorbance spectrum of 200 nm thick $SiN_x$ deposited on quartz (left trace), as well as a photoluminescence (PL) spectrum of 50-nm-thick freestanding $SiN_x$ under 532 nm laser excitation (right trace). From FIG. 1D it is clear that photoexcitation leads to PL; however, the quantum yield of this process at room temperature is low (~0.07, ref. 27) suggesting that most of the radiation absorbed by the $SiN_x$ is dissipated in the form of heat. Therefore, despite the weak absorption of 532 nm radiation by water, the heated $SiN_x$ instantly heats the nearby electrolyte, rapidly forming a steady-state thermal gradient that is localized near the membrane.

Example 3. Determination of Temperature of Heated Nanopore

A simulation was performed using a finite-element continuum approach.

Figure 1E:
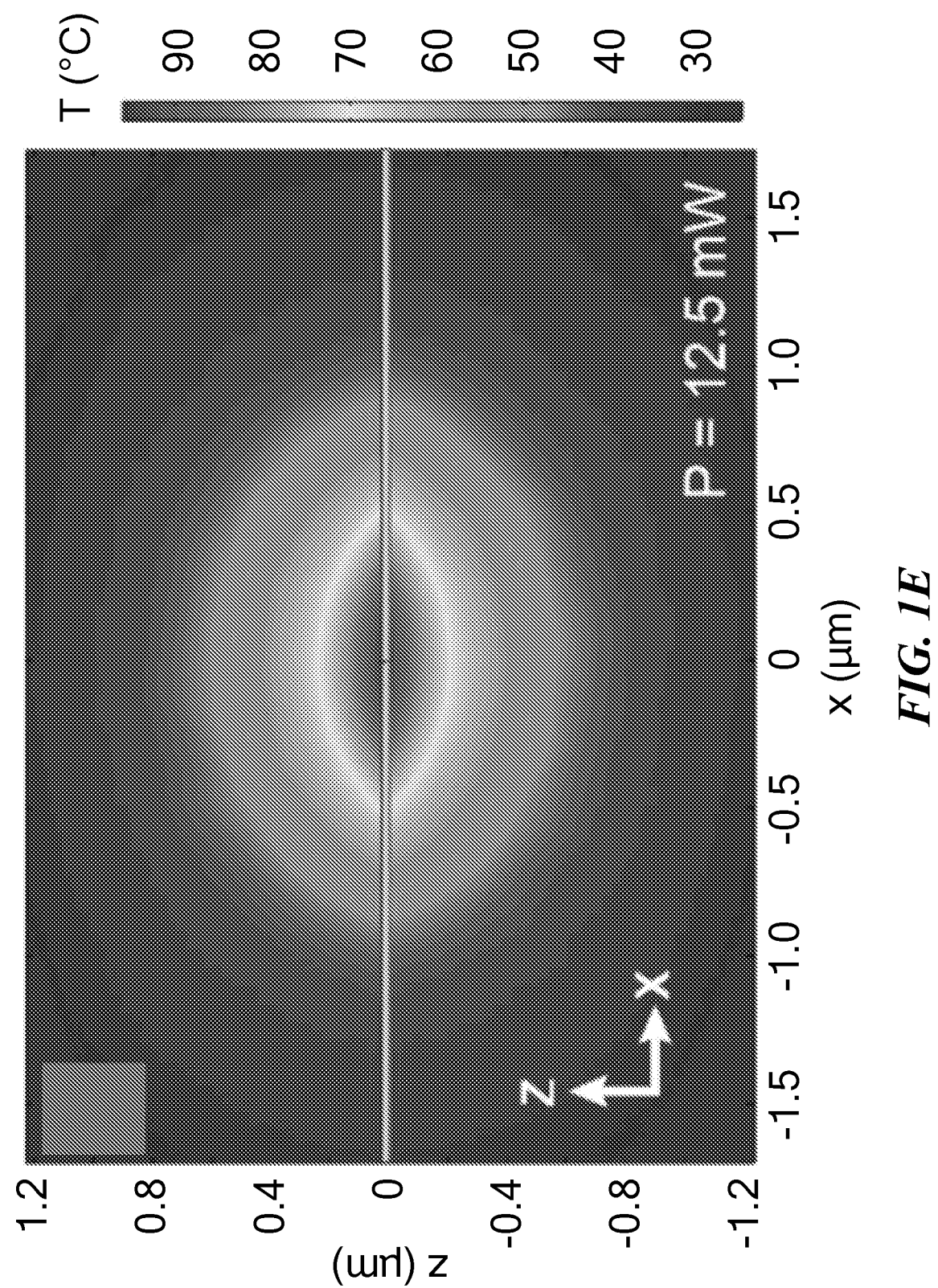

COMSOL Multiphysics software was used to analyze theoretically the laser-induced temperature increase and the impact of electrical force on melting temperature. For temperature calculations, a 42.5 nm thick $SiN_x$ membrane was modeled having a 3 nm diameter hourglass-shaped pore surrounded by electrolyte solution. Heat flux that corresponds to the laser power, after correcting for light reflection at all interfaces and photoluminescence emission, was applied from the bottom surface of the membrane. FIG. 1E displays a heat map of the calculated temperature surrounding a 43-nm-thick $SiN_x$ membrane with a 12.5 mW laser beam focused at the pore. The material properties and laser conditions were matched to the experimental setup conditions shown in FIG. 5A. It was further assumed that all radiation absorbed by the $SiN_x$, yet not resulting in PL, was dissipated as heat. This efficient localized heating of the nanoscale membrane interface results in significant temperature gradients that extend to hundreds of nanometers away from the membrane (see FIG. 5B). The peak temperature at the pore ($T_p$) for this simulation, corresponds to a thermal gradient ($\Delta T$) of approximately 70° C. (see FIG. 5C).

Example 4. Determination of Surface Charge of a Heated Nanopore

Figure 3A:
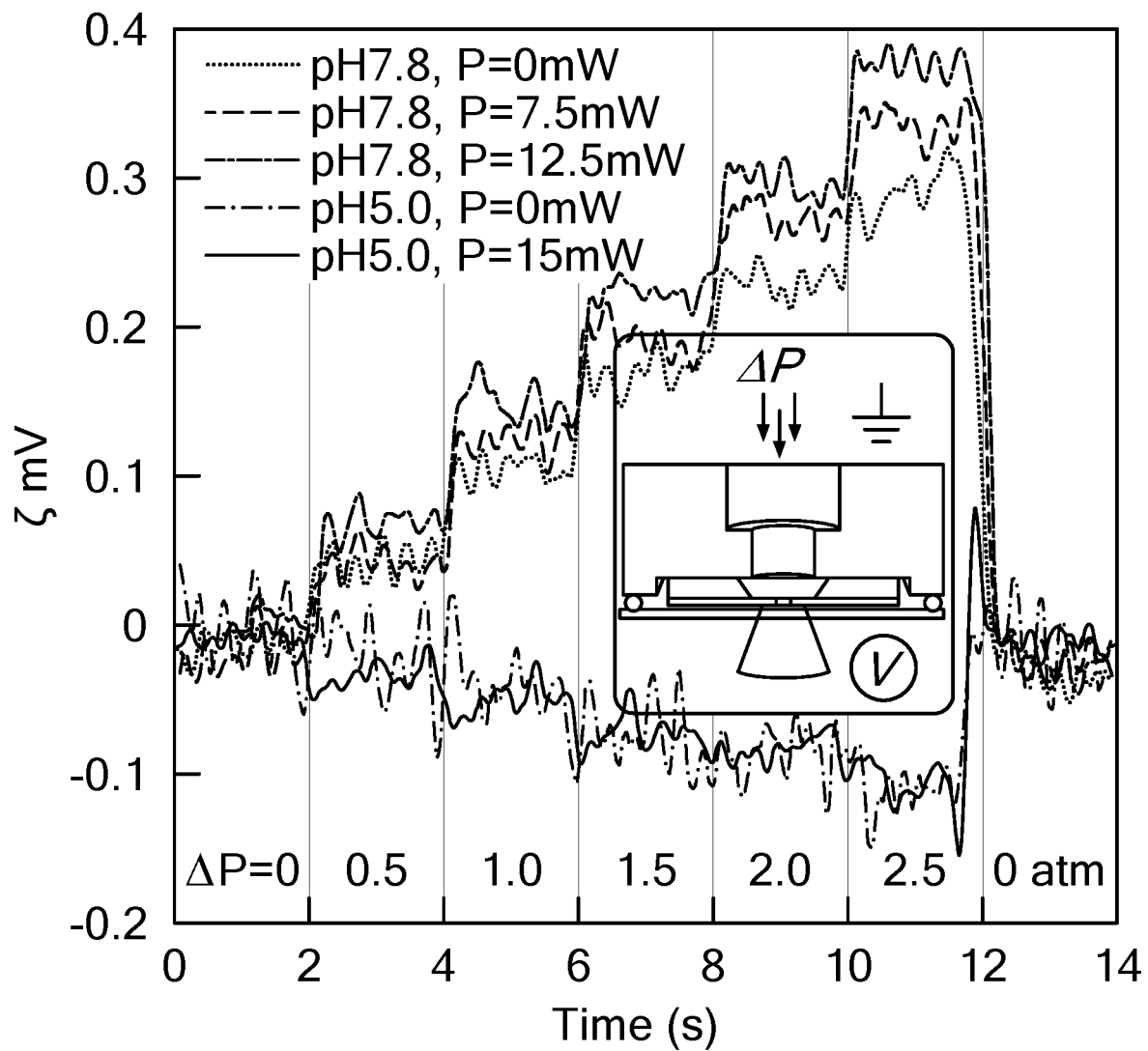
FIGS. 3A-3B show the results of nanopore surface charge measurements.
Figure 3B:
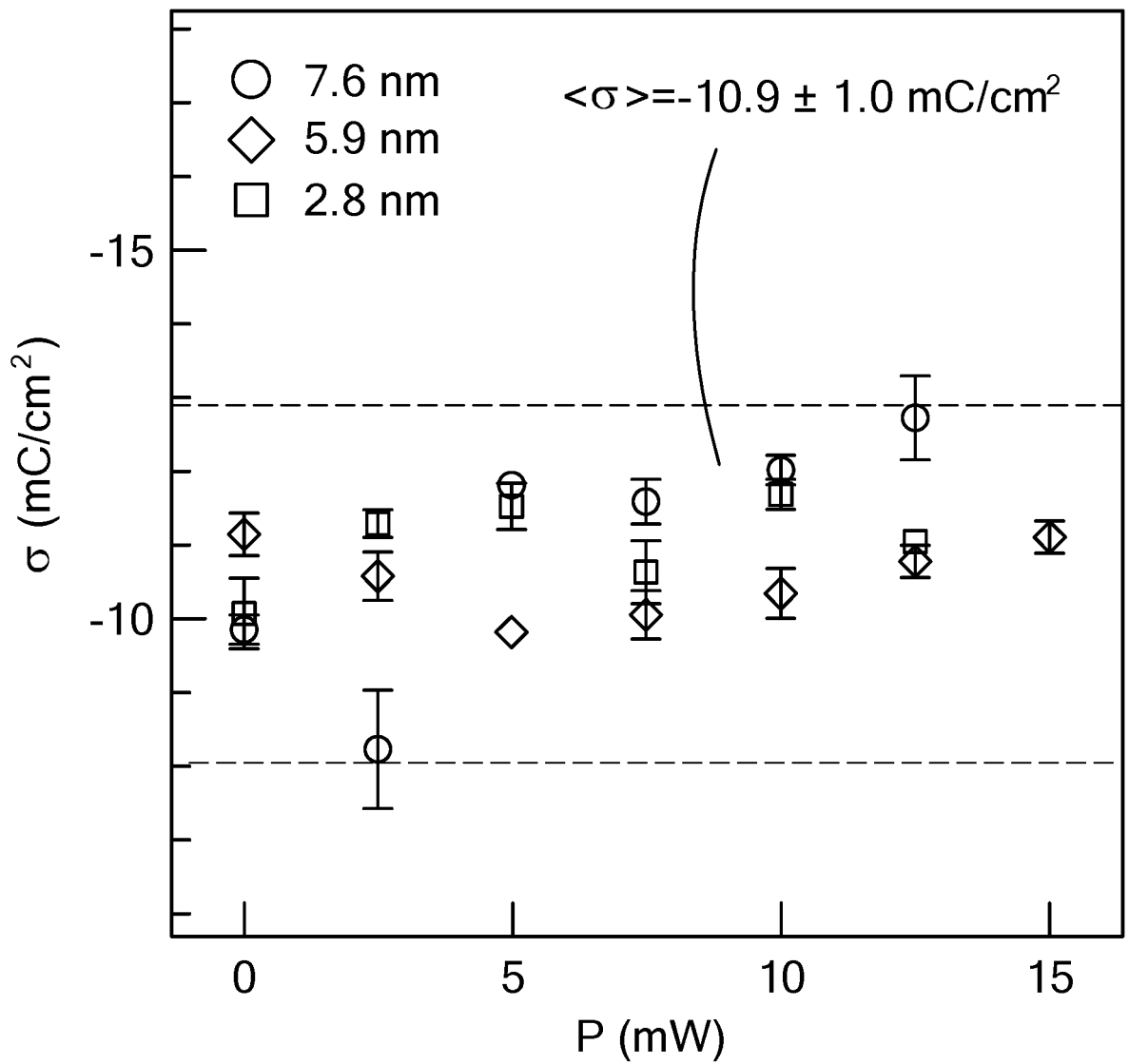

Apart from heating, increase of surface charge at the nanopore could theoretically lead to ion current enhancement upon laser irradiation of the pore. A recent study using a similar $SiN_x$ pore (26). To investigate this possibility, a cell was designed that allows pore surface charge to be measured during laser excitation. The cell allows a pressure gradient ($\Delta P$) to be applied to the cis chamber, facilitating streaming potential ($\zeta$) measurements (28,29). FIG. 3A shows exemplary traces of as a function of $\Delta P$ for different values of laser power (P) at the pore. These measurements were carried out at pH 7.8, the typical buffer conditions used in studies of nanopore heating presented herein, as well as pH 5.0, a more acidic condition that leads to $SiN_x$ surface charge inversion (28). Increasing $\Delta P$ led to increasingly more positive $\zeta$ values at pH 7.8, since a positive bias at the trans chamber is required to neutralize the pressure-driven counterion streaming current ($K^+$ ions). At pH 5.0, however, the opposite trend was seen, confirming surface charge inversion. More importantly, it was observed that $\zeta$ as a function of $\Delta P$ was relatively independent of P; that is, light did not appreciably impact the pore's surface charge. FIG. 3B shows a plot of the pore surface charge density ($\sigma$) as a function of P for three different $SiN_x$ pores at pH 7.8 with indicated diameters (see ref. 29 for details). For all experiments and all laser powers at pH 7.8, it was found that $\langle\sigma\rangle = -10.9\pm1.0$ $mC/cm^2$, whereas at pH 5.0 it was found that $\sigma=+2.2\pm0.3$ $mC/cm^2$ for P=0 mW and $\sigma=+2.7\pm0.2$ $mC/cm^2$ for P=15 mW. For the 7.6 nm pore, a changed by 30% upon maximum irradiation, which is expected to contribute to a less than 3% enhancement of the ion current (14). Given the observed enhancement of ion current of about 100% upon laser irradiation, the overwhelming mechanism that governs laser-induced ion current enhancement is a photothermal heating effect.

Example 5. Thermophoresis of Nucleic Acid Molecules at a Heated Nanopore

While the direct measurement of temperature at a nanopore is not practical, the relationship between pore conductance and electrolyte temperature has been previously studied in detail (23). As the solution temperature increases, its viscosity decreases, resulting in increased ion mobilities and increased pore conductance. FIG. 4A presents the fractional current enhancement, I(P)/I(0), as a function of laser power for a 3 nm diameter pore under 100 mV applied voltage. In bulk, the solution conductivity has been determined to increase linearly with temperature in the range 0-100° C., and the ion current can be expressed as a function of temperature using the following approximation, $$I(T)=A\sigma(T)=A(a+bT) \quad (1)$$

where A is a constant that depends on pore geometry and a and b are constants that depend on the electrolyte (23). The straight line in FIG. 4A represents the expected enhancement as a function of temperature for this pore, where the coefficients a and b are 2.4 and 0.125, respectively (30). Clearly, the experimental data (upper circles) deviates from the straight line defined by eq 1, as previously observed (26).

To explain the experimental result, eq 1 was refined by considering the effect of thermophoresis, which describes the diffusion of molecular species in a thermal gradient. Thermophoresis is a known effect in which species migrate in a thermal gradient due to the Soret effect. A species with a positive Soret coefficient ($S_T$) will diffuse toward a colder region, whereas a species with a negative value of $S_T$ will diffuse toward the hotter region (31). Since laser-induced heating causes a strong thermal gradient, the equilibrium ion concentration (C) at the pore should be affected by thermophoresis, an additive effect to thermal effects on solution conductivity. Thermodiffusion and the Soret coefficient are depicted as eqs 2 and 3, respectively:

$$C/C_0 = \exp[-S_T(T-T_{room})] \quad (2)$$

$$S_T = S_T^\infty\left[1-\exp\left[\frac{T^*-T}{T_0}\right]\right] \quad (3)$$

where $C_0$, $S_T$, $T_{room}$, $S_T^\infty$, $T^*$, and $T_0$ are the bulk species concentration, Soret coefficient, room temperature, a high-T thermophobic limit, the temperature where $S_T$ switches sign, and the strength of temperature effects, respectively (31,32). Combining eqs 1, 2, and 3, an expression is derived for the ionic current enhancement, defined as the current as a function of power I(P) normalized to the current without any laser applied I(0), as a function of local pore temperature:

$$I(P)/I(0) = I(T)/I(T_{room}) = C/C_0 \quad (4)$$
$$\left[\frac{a+b(\Delta T+T_{room})}{a+bT_{room}}\right]$$

The experimental data of FIG. 4A fit the model of eq 4 well, using the literature value of $S_T^\infty=0.0098$ $K^{-1}$ (33) and using fitting parameters for $T_0$ and $T^*$ for KCl we obtain values of $T_0=193\pm5.0$ K and $T^*=297\pm1.3$ K at room temperature ($T_{room}=295$ K). While the present value for $T_0$ is higher than literature values, $T^*$ is in good agreement with previous work (33). After fitting the data, the emerging relationship between I(P)/I(0) and the peak pore temperature ($T_p$) allowed the determination of pore temperature based on the current enhancement factor. The positive value of $S_T$ for KCl dictates a reduction in the relative ion concentration ($C/C_0$) at the pore as laser power increases. As comparison, a 28 nm pore with 16.5 nm thick $Al_2O_3$ and 5 nm thick $SiN_x$ membrane showed considerably low I(P)/I(0) as a function of laser power (see FIG. 4A, lower circles), which is attributed induction of heating by charge carriers in $SiN_x$. Also, laser power does not always produce the same enhancement from pore to pore, due to several factors that include variability in chemical composition of the pore, the exact focus position, and pore geometry.

Figure 4B:
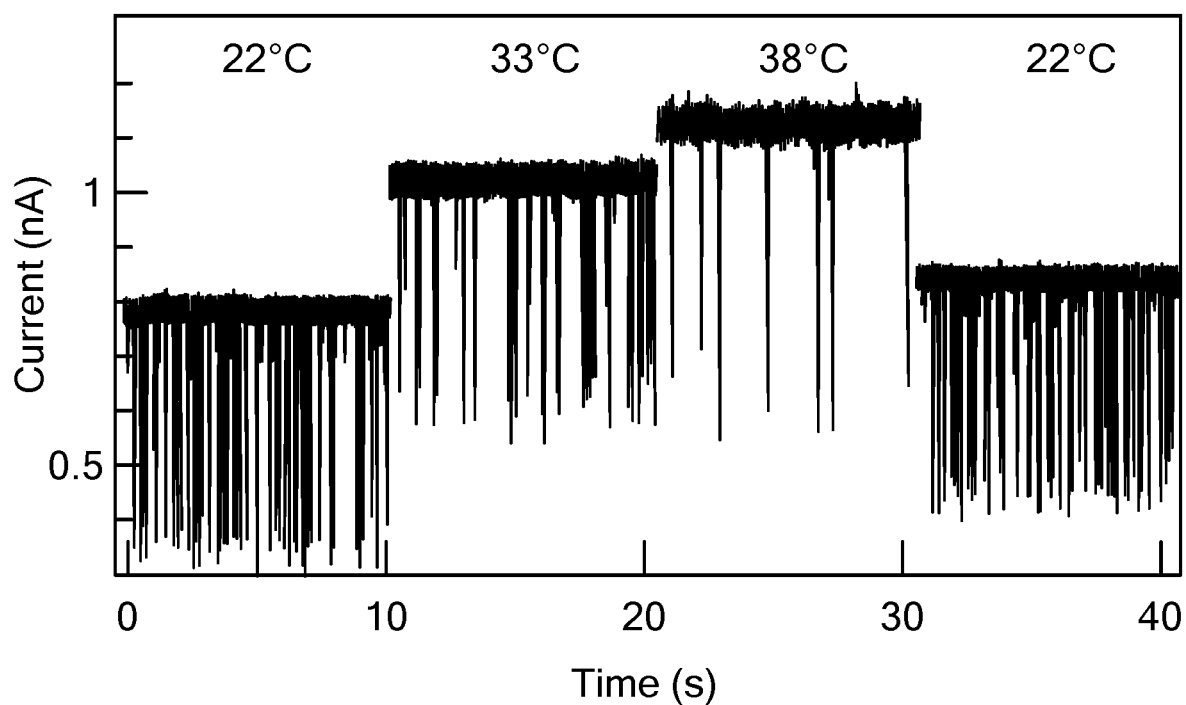
Figure 4C:
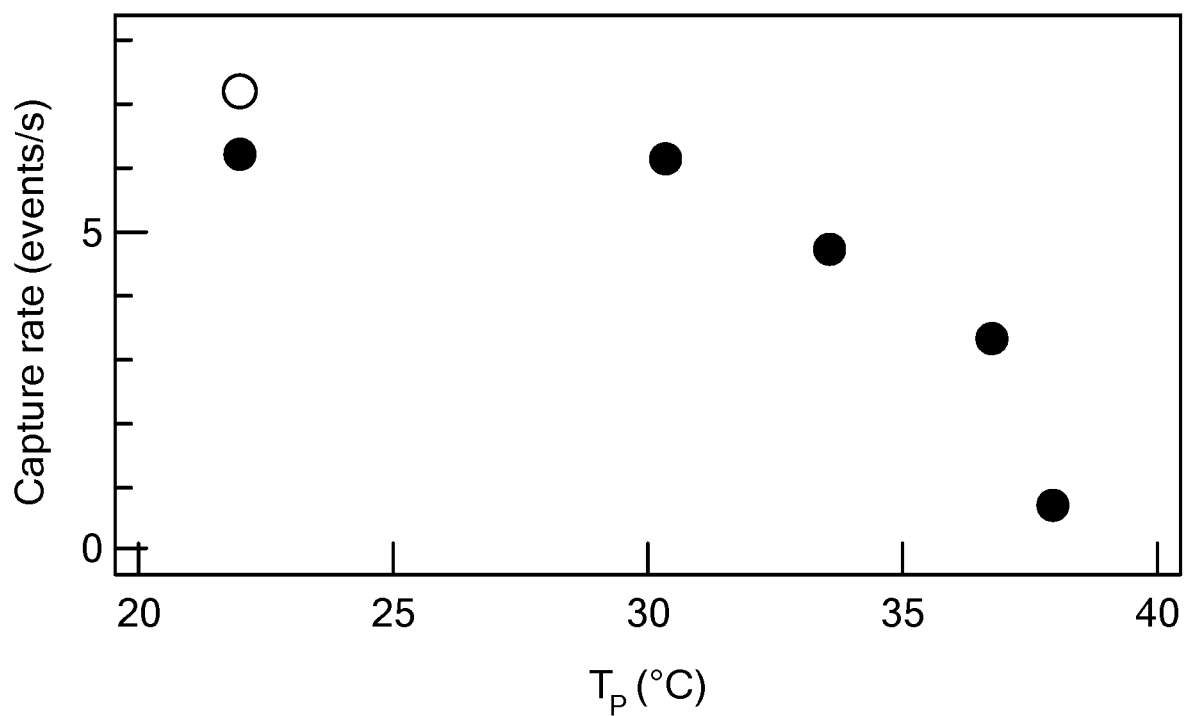

Further evidence for thermophoresis is seen by DNA capture behavior as a function of laser power. FIG. 4B shows sample current traces obtained for a 30 nM sample of 1 kbp dsDNA added to the cis chamber using a 4 nm diameter pore (V=200 mV) at different laser powers P. As P increased, a monotonic reduction in DNA capture rates was observed, which was restored to the original capture values when the laser was switched off (far right trace). This suggests a positive value of $S_T$ for DNA in KCl electrolyte, in accordance with a previous study using plasmonic heated pores (24). A summary of DNA capture rates vs. peak pore temperatures ($T_p$) is shown in FIG. 4C.

Example 6. Probing Nucleic Acid Secondary Structure Using Nanopore Heating

The role of temperature on nucleic acid secondary structure was investigated using laser-induced heating of a nanopore, and using nanopore current enhancement as a thermometer. FIG. 7A shows a series of 2 s long continuous current traces that depict the passage of Arg-tRNA molecules through a 3 nm pore at different temperatures in the range of 22-58° C. (V=600 mV), produced by altering the power of laser irradiation. The pore geometry requires deformation of intact tRNA molecules before their passage through the nanopore, while melted tRNA is more flexible and can smoothly pass through the pore (9,34). Dwell time ($t_d$) statistics therefore allow one to distinguish molecular deformation below and above the thermal melting transition. The traces in FIG. 7A show long dwell times for the Arg-tRNA near room temperature ($t_d$ values of >10 ms), whereas increasing the pore temperature ($T_p$) resulted in markedly reduced $t_d$ values (confirmed by scatter plots, not shown).

A similar experiment was carried out using a synthetic three-way junction (3WJ) DNA molecule, assembled from three DNA strands in a way that produces a branching site that melts at 37.5° C. (construct referred to as $3WJ_{37.5C}$) under the experimental buffer conditions used (for sequence and structure see FIG. 7D). The results are presented in FIG. 7B. As observed with Arg-tRNA, the transition in $t_d$ vs $T_p$ is evident from the pulse shapes for $3WJ_{37.5C}$ (confirmed by scatter plots, not shown).

A summary of $t_d$ vs. $T_p$ for the two nucleic acid molecules is shown in FIG. 7C, and reveals sharp transitions at $T^*_m$=38.3±0.5° C. and 33.0±1.0° C. for Arg-tRNA and $3WJ_{37.5C}$, respectively. Similarly pronounced transitions toward faster $t_d$ values were obtained in other experiments with a different pore (N=2 for tRNA and N=2 for 3WJ).

Figure 7E:
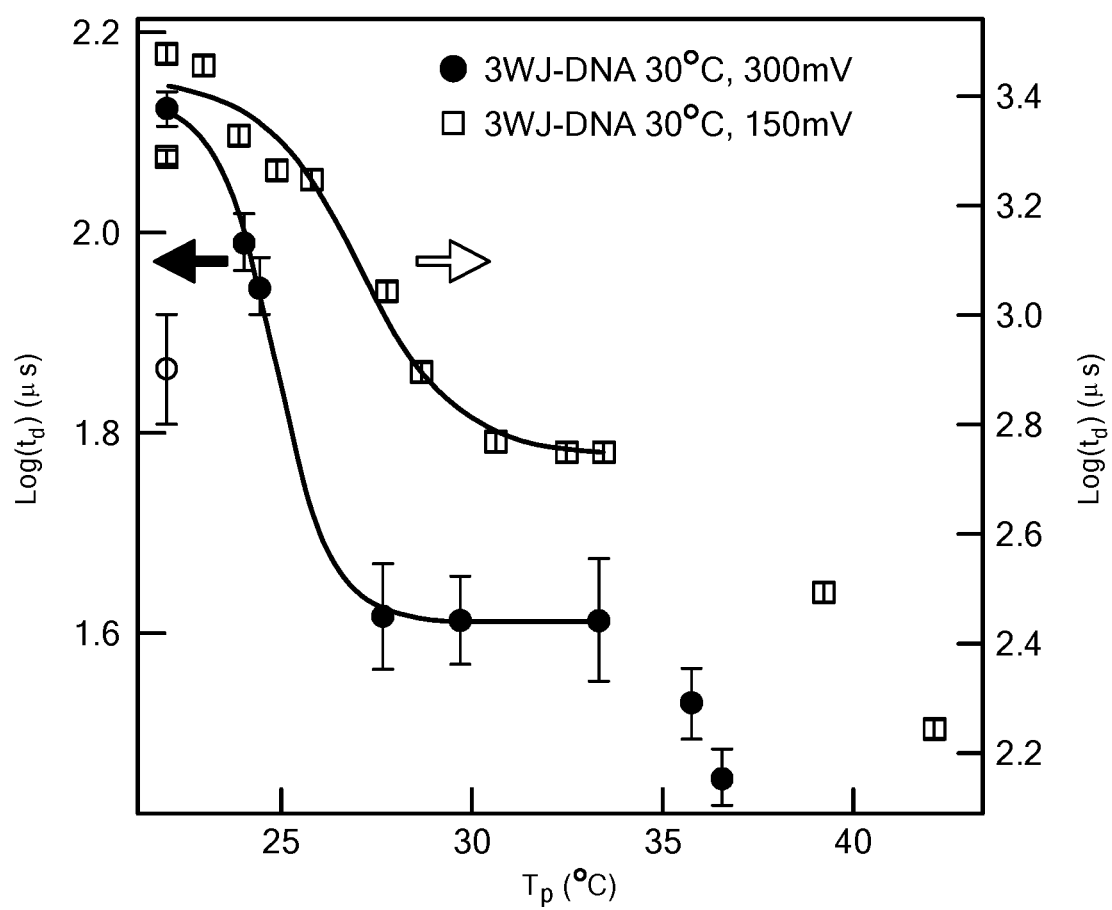

To further confirm that these measurements probe a thermal melting transition, another 3WJ DNA molecule was designed and tested, for which the melting temperature of a branching site is 30° C. (referred to as $3WJ_{30C}$). FIG. 7D shows the structure of this molecule compared to $3WJ_{37.5C}$, and FIG. 7E shows $t_d$ values vs $T_p$ for two different applied voltages. The observed transitions ($T^*_m$ of 24 and 27° C.) were lower than for $3WJ_{37.5C}$, consistent with the expected melting temperature trend. Further, considering that voltage is a force perturbation of the molecule that should reduce the melting temperature $T^*_m$, it is expected that increasing the voltage should reduce the melting temperature transition point.

Finally, as a negative control experiment against the data in FIG. 7E, the dwell times of a linear 1 kbp double-stranded DNA fragment were tested in the temperature range 22-38° C. The results are presented in FIG. 7F, and reveals only a mild reduction in dwell times without any observed transition.

Example 7. Effect of Applied Force on Nucleic Acid Melting Temperature

Force-induced impact on molecular melting transitions have been observed in AFM (35) and optical tweezers (36) measurements. For DNA melting, a finite change in heat capacity, $\Delta C_p$, between the native and melted state was found (37) which, after correction, yielded a predictable relationship between melting temperature and the applied force on the molecule (36). In the case where $\Delta C_p$=0, a linear relationship between applied force and melting temperature is expected, which allows extrapolation of thermal melting vs. force to obtain the zero-force melting temperature of the molecule. To test this, melting transition data for the molecule are needed at different forces, which, based on the approach in FIGS. 7A-F, would require dwell-time data for several voltages at each temperature, totaling 30-40 data sets. This limitation was overcome by developing a thermoscopic method for probing thermal melting in a single molecule. In this alternative approach, the molecule is rapidly heated only after its capture in the pore, and thereafter its melting dynamics are probed.

The approach taken is analogous to nanopore force spectroscopy in which detection of molecular capture in the pore triggers an immediate voltage ramp (38-41). However, in the present case, molecular capture in the pore sends a voltage waveform to the electro-optic modulator within 4 µs, which results in a prescribed laser power schedule that heats the individual molecule that is probed at the pore. FIG. 8A shows a representative set of traces obtained using this method for Arg-tRNA. Normalized current traces are overlaid such that capture occurs at t=0 ms, also the point at which the laser is swept to allow single-molecule heating. The fluctuating current signals in region 2 are believed to reflect the molecule's dynamics in the pore as a function of temperature prior to melting, whereas melting has occurred when the current is restored to its increasing baseline value, clearly seen at the time shown by the arrow, which marks the beginning of region 3 shown above for the highlighted trace. Pore thermometry was achieved from the open-pore ion current.

FIG. 8B shows histograms of melting times/temperatures obtained for four different voltages. From the mean values of these histograms, a plot of the average tRNA melting temperature as a function of applied voltage was constructed and is shown in FIG. 8C. Using the fact that literature values of $\Delta C_p$ for Phe-tRNA are negligible under similar ionic strengths ($\Delta C_p$=0 at 150 mM NaCl, ref. 42), linearity was assumed between the applied force and melting transition temperature (36). The resulting linear fit to the data yielded an ordinate intercept of 63.2° C., in very close agreement to tRNA melting temperature of 62° C. in 0.5 M NaCl (43). It is noted that the information-rich approach of thermoscopy required four data sets at different voltages to achieve equilibrium melting point determination, in contrast to the many data sets required in the approach of point-by-point static temperature experiments shown in FIGS. 7A-F.

Finally, for the $3WJ_{30C}$ data in FIG. 7E that contains two voltage points, if $\Delta C_p$ is neglected for the molecule, a crude melting temperature estimate of 30° C. is obtained, in excellent agreement with the bulk measurements.

As used herein, "consisting essentially of" allows the inclusion of materials or steps that do not materially affect the basic and novel characteristics of the claim. Any recitation herein of the term "comprising", particularly in a description of components of a composition or in a description of elements of a device, can be exchanged with "consisting essentially of" or "consisting of".

While the present technology has been described in conjunction with certain preferred embodiments, one of ordinary skill, after reading the foregoing specification, will be able to effect various changes, substitutions of equivalents, and other alterations to the compositions and methods set forth herein.

REFERENCES (1) Dekker, C. Nat. Nanotechnol. 2007, 2, 209-215.
(2) Venkatesan, B. M.; Bashir, R. Nat. Nanotechnol. 2011, 6, 615-624.
(3) Wanunu, M. Phys. Life Rev. 2012, 9, 125-158.
(4) Shi, W.; Friedman, A. K.; Baker, L. A. Anal. Chem. 2017, 89, 157-188.
(5) Kasianowicz, J. J.; Bezrukov, S. M. Biophys. J. 1995, 69, 94-105.
(6) DeBlois, R. W.; Bean, C. P. Rev. Sci. Instrum. 1970, 41, 909-916.
(7) Sauer-Budge, A. F.; Nyamwanda, J. A.; Lubensky, D. K.; Branton, D. Phys. Rev. Lett. 2003, 90, 238101.
(8) Shasha, C.; Henley, R. Y.; Stoloff, D. H.; Rynearson, K. D.; Hermann, T.; Wanunu, M. ACS Nano 2014, 8, 6425-6430.
(9) Henley, R. Y.; Ashcroft, B. A.; Farrell, I.; Cooperman, B. S.; Lindsay, S. M.; Wanunu, M. Nano Lett. 2016, 16, 138-144.
(10) Manrao, E. A.; Derrington, I. M.; Laszlo, A. H.; Langford, K. W.; Hopper, M. K.; Gillgren, N.; Pavlenok, M.; Niederweis, M.; Gundlach, J. H. Nat. Biotechnol. 2012, 30, 349-353.
(11) Garalde, D. R.; Snell, E. A.; Jachimowicz, D.; Heron, A. J.; Bruce, M.; Lloyd, J.; Warland, A.; Pantic, N.; Admassu, T.; Ciccone, J.; Serra, S.; Keenan, J.; Martin, S.; McNeill, L.; Wallace, J.; Jayasinghe, L.; Wright, C.; Blasco, J.; Sipos, B.; Young, S.; Juul, S.; Clarke, J.; Turner, D. J. bioRxiv. 2016.
(12) Henrickson, S. E.; Misakian, M.; Robertson, B.; Kasianowicz, J. J. Phys. Rev. Lett. 2000, 85, 3057-3060.
(13) Meller, A.; Nivon, L.; Branton, D. Phys. Rev. Lett. 2001, 86, 3435-3438.
(14) Smeets, R. M. M.; Keyser, U. F.; Krapf, D.; Wu, M.-Y.; Dekker, N. H.; Dekker, C. Nano Lett. 2006, 6, 89-95.
(15) Lu, B.; Hoogerheide, D. P.; Zhao, Q.; Zhang, H.; Tang, Z.; Yu, D.; Golovchenko, J. A. Nano Lett. 2013, 13, 3048-3052.
(16) Wanunu, M.; Sutin, J.; McNally, B.; Chow, A.; Meller, A. Biophys. J. 2008, 95, 4716-4725.
(17) Holmstrom, E. D.; Dupuis, N. F.; Nesbitt, D. J. Biophys. J. 2014, 106, 220-231.
(18) Hirsch, L. R.; Stafford, R. J.; Bankson, J. A.; Sershen, S. R.; Rivera, B.; Price, R. E.; Hazle, J. D.; Halas, N. J.; West, J. L. Proc. Natl. Acad. Sci. U.S.A 2003, 100, 13549-13554.
(19) Reiner, J. E.; Robertson, J. W. F.; Burden, D. L.; Burden, L. K.; Balijepalli, A.; Kasianowicz, J. J. J. Am. Chem. Soc. 2013, 135, 3087-3094.
(20) Angevine, C. E.; Seashols-Williams, S. J.; Reiner, J. E. Anal. Chem. 2016, 88, 2645-2651.
(21) Keyser, U. F.; Krapf, D.; Koeleman, B. N.; Smeets, R. M. M.; Dekker, N. H.; Dekker, C. Nano Lett. 2005, 5, 2253-2256.
(22) Smeets, R. M. M.; Keyser, U. F.; Wu, M. Y.; Dekker, N. H.; Dekker, C. Phys. Rev. Lett. 2006, 97, 088101.
(23) Jonsson, M. P.; Dekker, C. Nano Lett. 2013, 13, 1029-1033.
(24) Nicoli, F.; Verschueren, D.; Klein, M.; Dekker, C.; Jonsson, M. P. Nano Lett. 2014, 14, 6917-6925.
(25) Li, Y.; Nicoli, F.; Chen, C.; Lagae, L.; Groeseneken, G.; Stakenborg, T.; Zandbergen, H. W.; Dekker, C.; Van Dorpe, P.; Jonsson, M. P. Nano Lett. 2015, 15, 776-782.
(26) Di Fiori, N.; Squires, A.; Bar, D.; Gilboa, T.; Moustakas, T. D.; Meller, A. Nat. Nanotechnol. 2013, 8, 946-951.
(27) Giorgis, F.; Vinegoni, C.; Pavesi, L. Phys. Rev. B: Condens. Matter Mater. Phys. 2000, 61, 4693-4698.
(28) Firnkes, M.; Pedone, D.; Knezevic, J.; Döblinger, M.; Rant, U. Nano Lett. 2010, 10, 2162-2167.
(29) Waduge, P.; Hu, R.; Bandarkar, P.; Yamazaki, H.; Cressiot, B.; Zhao, Q.; Whitford, P. C.; Wanunu, M. ACS Nano 2017, 11, 5706.
(30) Pezeshki, S.; Chimerel, C.; Bessonov, A. N.; Winterhalter, M.; Kleinekathöfer, U. Biophys. J. 2009, 97, 1898-1906.
(31) Duhr, S.; Braun, D. Phys. Rev. Lett. 2006, 96, 168301.
(32) Iacopini, S.; Rusconi, R.; Piazza, R. Eur. Phys. J. E: Soft Matter Biol. Phys. 2006, 19, 59-67.
(33) Römer, F.; Wang, Z.; Wiegand, S.; Bresme, F. J. Phys. Chem. B 2013, 117, 8209-8222.
(34) Wanunu, M.; Dadosh, T.; Ray, V.; Jin, J.; McReynolds, L.; Drndic, M. Nat. Nanotechnol. 2010, 5, 807-814.
(35) Clausen-Schaumann, H.; Rief, M.; Tolksdorf, C.; Gaub, H. E. Biophys. J. 2000, 78, 1997-2007.
(36) Williams, M. C.; Wenner, J. R.; Rouzina, I.; Bloomfield, V. A. Biophys. J. 2001, 80, 1932-1939.
(37) Chalikian, T. V.; Völker, J.; Plum, G. E.; Breslauer, K. J. Proc. Natl. Acad. Sci. U.S.A 1999, 96, 7853-7858.
(38) Bates, M.; Burns, M.; Meller, A. Biophys. J. 2003, 84, 2366-2372.
(39) Mathé, J.; Arinstein, A.; Rabin, Y.; Meller, A. Europhys. Lett. 2006, 73, 128.
(40) Tropini, C.; Marziali, A. Biophys. J. 2007, 92, 1632-1637.
(41) Langecker, M.; Ivankin, A.; Carson, S.; Kinney, S. R. M.; Simmel, F. C.; Wanunu, M. Nano Lett. 2015, 15, 783-790.
(42) Hinz, H.-J.; Filimonov, V. V.; Privalov, P. L. Eur. J. Biochem. 1977, 72, 79-86.
(43) Riesner, D.; Maass, G.; Thiebe, R.; Philippsen, P.; Zachau, H. G. Eur. J. Biochem. 1973, 36, 76-88.
(44) Carson, S.; Wilson, J.; Aksimentiev, A.; Wanunu, M. Biophys. J. 2014, 107, 2381-93.
(45) Zadeh, J. N.; Steenberg, C. D.; Bois, J. S.; Wolfe, B. R.; Pierce, 590 M. B.; Khan, A. R.; Dirks, R. M.; Pierce, N. A. J. Comput. Chem. 2011, 32, 170-173.

What is claimed is:

1. A temperature controlled single molecule bioreactor system comprising a device for selective heating of a nanoscale environment, the device comprising:
   a solid state material in contact with the nanoscale environment;
   a laser having an emission wavelength falling within an absorption band of the solid state material; and
   one or more optical elements for focusing light from the laser selectively on the nanoscale environment;
   wherein irradiation of the solid state material with the laser results in selective heating of the nanoscale environment by the solid state material.

2. A method of selectively heating a nanoscale environment, the method comprising the steps of:

(a) providing the device of claim 1;
(b) irradiating the solid state material with light from the laser, whereby the light is absorbed by the solid state material and the nanoscale environment is selectively heated.

3. The method of claim 2, wherein the nanoscale environment extends over a volume from about 1 nm$^3$ to about 10$^9$ nm$^3$ and is heated by about 10° C. to about 90° C.

4. The method of claim 2, wherein the nanoscale environment contains a molecule, a macromolecular complex, a nanoparticle, a virus, or a cell that is heated.

5. The method of claim 4, wherein a single molecule is heated, and the molecule is a nucleic acid, protein, enzyme, nucleic acid polymerase, or DNA origami structure.

6. The method of claim 5, wherein the molecule is a nucleic acid and the method further comprises carrying out a single molecule PCR reaction using the nucleic acid molecule.

7. The method of claim 2, further comprising monitoring the temperature of the nanoscale environment.

8. The method of claim 7, wherein the nanoscale environment comprises a nanopore and temperature is monitored by measuring conductance through the nanopore.

9. The method of claim 2, wherein heating to a new steady state temperature occurs within less than 10 microseconds after starting the laser illumination of the solid state material.

10. The method of claim 2, wherein a structural rearrangement, folding, or unfolding of a molecule in the nanoscale environment is determined.

11. The method of claim 10, wherein a conformational change of a molecule in the nanoscale environment is determined using fluorescence resonance energy transfer (FRET).

12. The method of claim 2, wherein the intensity of laser illumination is modulated, resulting in modulation of temperature of the nanoscale environment.

13. The method of claim 12, wherein the solid state material is irradiated using a ramp of increasing laser intensity and results in a ramp of increasing temperature of the nanoscale environment.

14. The method of claim 12, wherein a melting temperature of a nucleic acid molecule in the nanoscale environment is determined.

15. The method of claim 2, wherein step (b) is repeated so as to separately heat two or more different nanoscale environments.

16. The method of claim 2, wherein single molecule sequencing at a nanopore is performed on one or more nucleic acid molecules at a temperature above ambient temperature.

17. A temperature controlled single molecule nucleic acid sequencing system comprising the device of claim 1.

18. A temperature controlled atomic force microscope (AFM) comprising the device of claim 1, wherein the laser is aligned with the axis of the AFM probe.

19. A temperature-activated DNA chip fabrication system comprising the device of claim 1.

\* \* \* \* \*